United States Patent
Kabanov et al.

(10) Patent No.: US 10,022,325 B2
(45) Date of Patent: Jul. 17, 2018

(54) COMPOSITIONS AND METHODS FOR THE TREATMENT OF CANCER

(71) Applicant: Board of Regents of the University of Nebraska, Lincoln, NE (US)

(72) Inventors: Alexander V. Kabanov, Chapel Hill, NC (US); Daria Y. Alakhova, Omaha, NE (US); Yi Zhao, Omaha, NE (US)

(73) Assignee: Board of Regents of the University of Nebraska, Lincoln, NE (US)

( * ) Notice: Subject to any disclaimer, the term of this patent is extended or adjusted under 35 U.S.C. 154(b) by 0 days.

(21) Appl. No.: 13/783,991

(22) Filed: Mar. 4, 2013

(65) Prior Publication Data

US 2013/0195964 A1 Aug. 1, 2013

Related U.S. Application Data

(63) Continuation-in-part of application No. PCT/US2011/050518, filed on Sep. 6, 2011.

(60) Provisional application No. 61/379,882, filed on Sep. 3, 2010.

(51) Int. Cl.
| | |
|---|---|
| *A61K 9/127* | (2006.01) |
| *A61K 47/10* | (2017.01) |
| *A61K 9/00* | (2006.01) |
| *A61K 31/704* | (2006.01) |

(52) U.S. Cl.
CPC ............ *A61K 9/127* (2013.01); *A61K 9/0019* (2013.01); *A61K 31/704* (2013.01); *A61K 47/10* (2013.01)

(58) Field of Classification Search
CPC . A61B 2562/12; A61B 5/0035; A61B 5/0095; A61B 5/7278; A61B 8/4416; A61B 8/4444; A61K 31/704; A61K 47/10; A61K 9/0019; A61K 9/127; F04C 2270/041; G01N 21/1702; G06F 17/10; G06F 17/50
See application file for complete search history.

(56) References Cited

U.S. PATENT DOCUMENTS

| | | | |
|---|---|---|---|
| 7,422,875 B2 | 9/2008 | Kabanov et al. | |
| 8,535,656 B2 | 9/2013 | Kabanov et al. | |
| 2005/0003008 A1* | 1/2005 | Rapoport ............. | A61K 9/1075 424/486 |
| 2008/0075762 A1* | 3/2008 | Tardi ................... | A61K 9/0019 424/450 |
| 2008/0181939 A1 | 7/2008 | Discher et al. | |
| 2008/0206187 A1 | 8/2008 | Exner et al. | |

FOREIGN PATENT DOCUMENTS

| | | |
|---|---|---|
| WO | 2008/141155 | 11/2008 |
| WO | 2011/127256 | 10/2011 |

OTHER PUBLICATIONS

Trosko (Mutation Research, 480-481 (2001), 219-229).*
Alakhov et al. (Bioconjugate Chem 1996, 7, 209-216).*
Zhao et al., A Simple Way to Enhance Doxil® Therapy: Drug Release from Liposomes at the Tumor Site by Amphiphilic Block Copolymer, Journal of Controlled Release, May 28, 2013, pp. 61-69, 168(1).
Alakhova et al., Differential Metabolic Responses to Pluronic in MDR and Non-MDR Cells: A Novel Pathway for Chemosensitization of Drug Resistant Cancers, Journal of Controlled Release, Feb. 25, 2010, pp. 89-100, 142 (1).
Batrakova et al., Sensitization of Cells Overexpressing Multidrug Resistant Proteins by Pluronic P85, Pharmaceutical Research, Oct. 2003, pp. 1581-1590, 20(10).
Batrakova et al., Effects of Pluronic and Doxorubicin on Drug Uptake, Cellular Metabolism, Apoptosis and Tumor Inhibition in Animal Models of MDR Cancers, Journal of Controlled Release, May 10, 2010, pp. 290-301, 143(3).
Kabanov et al., An Essential Relationship Between ATP Depletion and Chemosensitizing Activity of Pluronic® Block Copolymers, Journal of Controlled Release, Aug. 28, 2003, pp. 75-83, 91(0).
Bae et al., Targeted Drug Delivery to Tumors: Myths, Reality and Possibility, Journal of Controlled Release, Aug. 10, 2011, pp. 198-205, 153(3).
Kwon et al., Analysis on the Current Status of Targeted Drug Delivery to Tumors, Journal of Controlled Release, Dec. 10, 2012, pp. 61-69, 164(2).
Vail, D.M., et al., "Pegylated Liposomal Doxorubicin: Proof of Principle Using Preclinical Animal Models and Pharmacokinetic Studies" Semin. Oncol. (2004) 31(Suppl 13):16-35.
Boulikas, T., "Clinical Overview on Lipoplatin: A Successful Liposomal Formulation of Cisplatin" Expert Opin. Investig. Drugs (2009) 18(8):1197-218.
Gokhale, P.C., et al., "Improved Safety, Pharmacokinetics and Therapeutic Efficacy Profiles of a Novel Liposomal Formulation of Mitoxantrone" Anticancer Res. (2001) 21(5):3313-21 [Abstract only].
Koudelka, S., et al., "Liposomal Paclitaxel Formulations" J. Controlled Rel. (2012) 163:322-334.
Leonetti, C., et al., "In Vivo Administration of Liposomal Vincristine Sensitizes Drug-Resistant Human Solid Tumors" Int. J. Cancer (2004) 110:767-774.
Petre, C.E, et al., "Liposomal Daunorubicin as Treatment for Kaposi's Sarcoma" Intl. J. Nanomed. (2007) 2 (3):277-288.

* cited by examiner

*Primary Examiner* — Snigdha Maewall
(74) *Attorney, Agent, or Firm* — Robert C. Netter, Jr.; Dann, Dorfman, Herrell and Skillman, P.C.

(57) ABSTRACT

The present invention provides compositions and methods for the treatment of cancer are provided.

8 Claims, 16 Drawing Sheets

A

B

COMPOSITIONS AND METHODS FOR THE TREATMENT OF CANCER

Figure 1A:
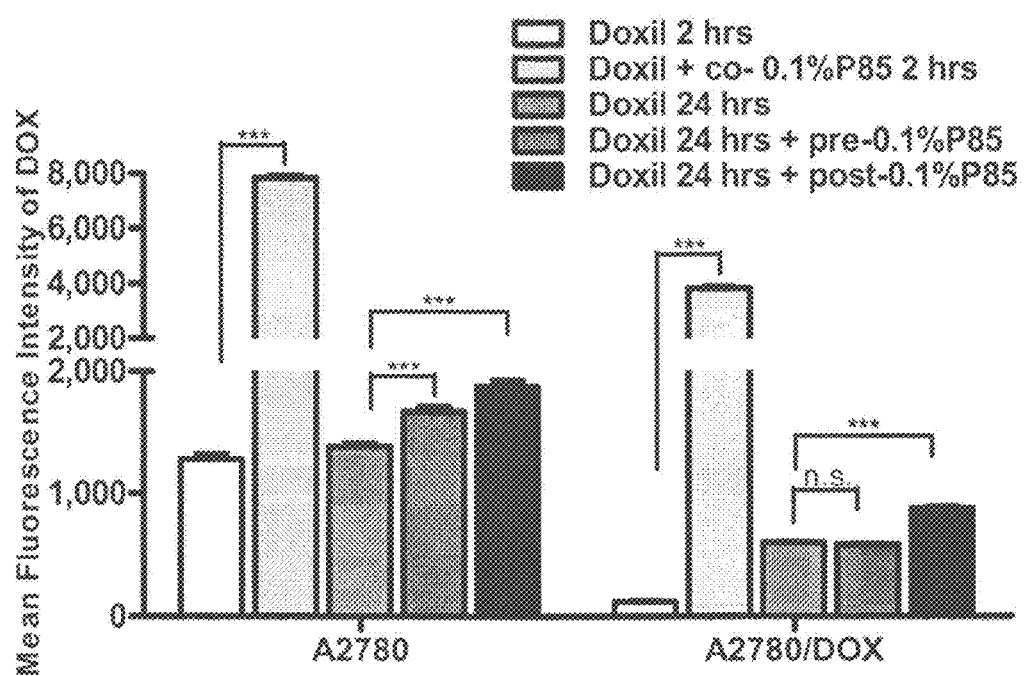

This application is a continuation-in-part of PCT/US2011/050518, filed on Sep. 6, 2011, which claims priority under 35 U.S.C. § 119(e) to U.S. Provisional Patent Application No. 61/379,882, filed on Sep. 3, 2010. The foregoing applications are incorporated by reference herein.

This invention was made with government support under Grant No. 2R01 CA89225 awarded by the National Institutes of Health. The government has certain rights in the invention.

FIELD OF THE INVENTION

The present invention relates generally to cancer therapies. More specifically, the present invention provides compositions and methods for the improved delivery of therapeutic agents to a patient for the treatment of cancer.

BACKGROUND OF THE INVENTION

DOXIL® (doxorubicin HCl liposome injection) significantly reduces the side effects associated with doxorubicin. The need to administer DOXIL® only once every 4 weeks by intravenous administration also makes DOXIL® convenient for patients. However, DOXIL® has been shown to not be as effective as doxorubicin. Accordingly, means for increasing the therapeutic efficacy of DOXIL®, while preserving its safety, are desirous.

SUMMARY OF THE INVENTION

In accordance with the instant invention, methods of inhibiting cancer in a subject are provided. In a particular embodiment, the method comprises administering at least one encapsulated chemotherapeutic agent and at least one amphiphilic block copolymer to the subject. The encapsulated chemotherapeutic agent and the amphiphilic block copolymer may be administered simultaneously and/or sequentially, particularly when the encapsulated therapeutic is administered first. In a particular embodiment, the encapsulated chemotherapeutic agent is a liposomal doxorubicin. In a particular embodiment, the amphiphilic block copolymer comprises at least one block of ethylene oxide and at least one block of propylene oxide.

In accordance with another aspect of the instant invention, compositions comprising at least one encapsulated chemotherapeutic agent, at least one amphiphilic block copolymer, and at least one pharmaceutical carrier are provided. Kits comprising a) a first composition comprising at least one encapsulated chemotherapeutic agent and at least one pharmaceutical composition; and b) a second composition comprising at least one amphiphilic block copolymer and at least one pharmaceutical composition, are also provided.

BRIEF DESCRIPTIONS OF THE DRAWING

Figure 1B:
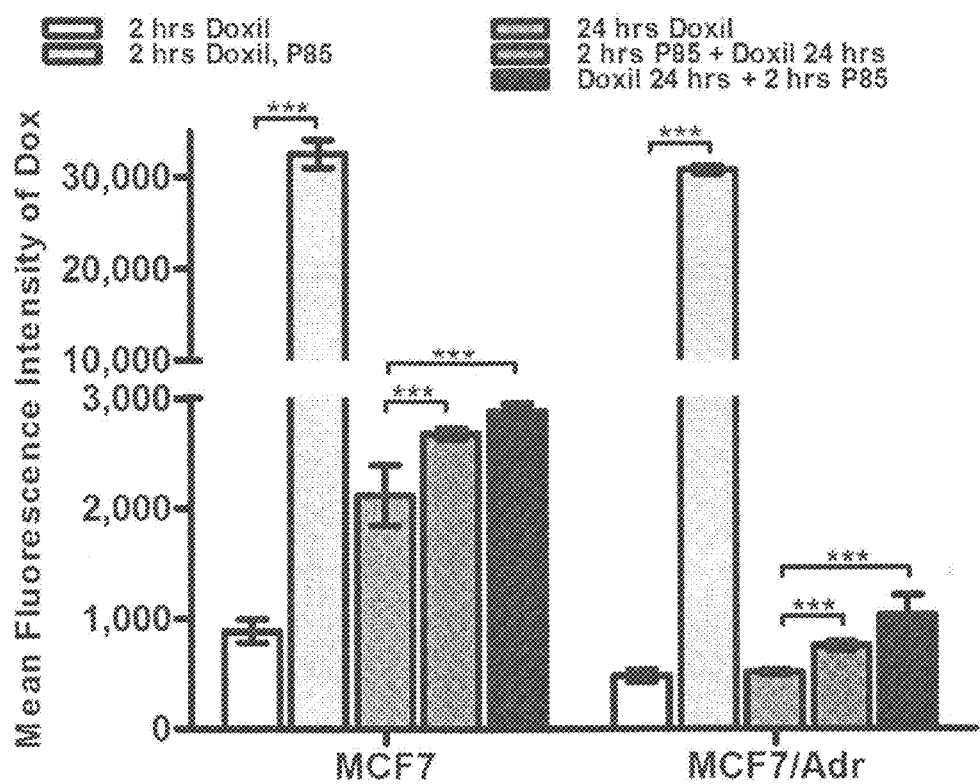

FIGS. 1A and 1B show the cellular uptake of Doxil® formulations in ovarian and breast cancer cells, respectively. DOX mean fluorescence intensity was counted by flow cytometry. Cells were treated with 1) Doxil® alone for 2 hours; 2) Doxil® and 0.1% P85 co-treatment for 2 hours, 3) Doxil® alone for 24 hours; 4) first treated with 0.1% P85 for 2 hours, washed three times with PBS and further incubated with Doxil® for 24 hours; and 5) first treated with Doxil® for 24 hours, washed three times with PBS, followed by 2 hours treatment with 0.1% P85. Data are mean±SEM (n=6), * p<0.05, n.s. stands for no significance. The p values were obtained using Student's t-test following logarithmic transformation of the data.

Figure 2:
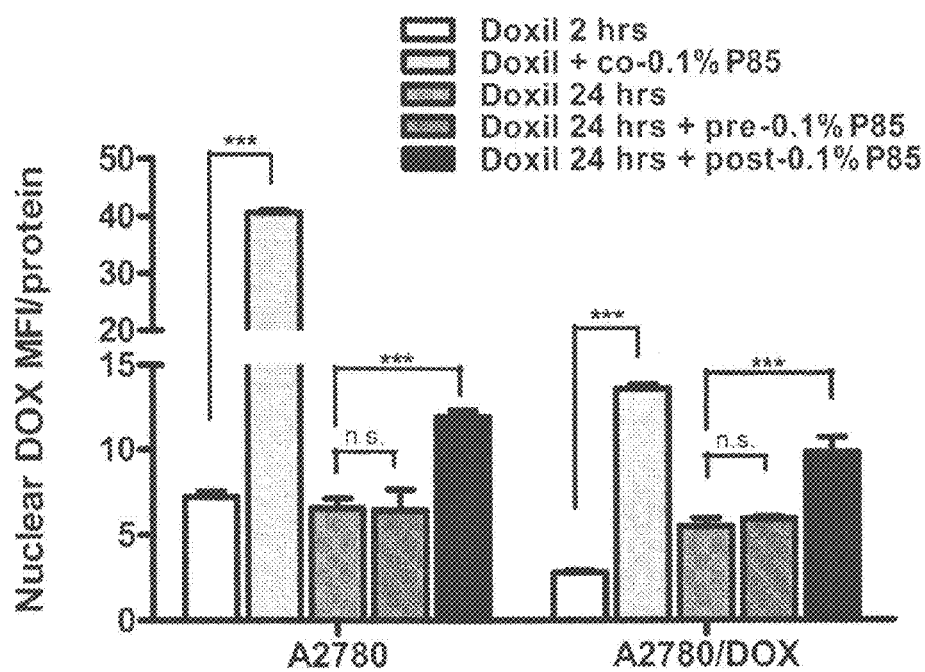

FIG. 2 shows the nuclear uptake of Doxil® formulations in ovarian cancer cells. Cells were treated with 1) Doxil®; 2) Doxil® and 0.1% P85 co-treatment for 2 hours, 3) first treated with 0.1% P85 for 2 hours, washed three times with PBS and further incubated with Doxil® for 24 hours; 4) first treated with Doxil® for 24 hours, washed three times with PBS, followed by 2 hours treatment with 0.1% P85. After treatment the cells were washed three times with PBS, lyzed using M-PER lysis buffer and Dox fluorescence was measured using SpectaMax® MS plate reader and normalized over protein content. Data are mean±SEM (n=6), *** p<0.05, n.s. stands for no significance. The p values were obtained using Student's t-test following logarithmic transformation of the data.

Figure 3A:
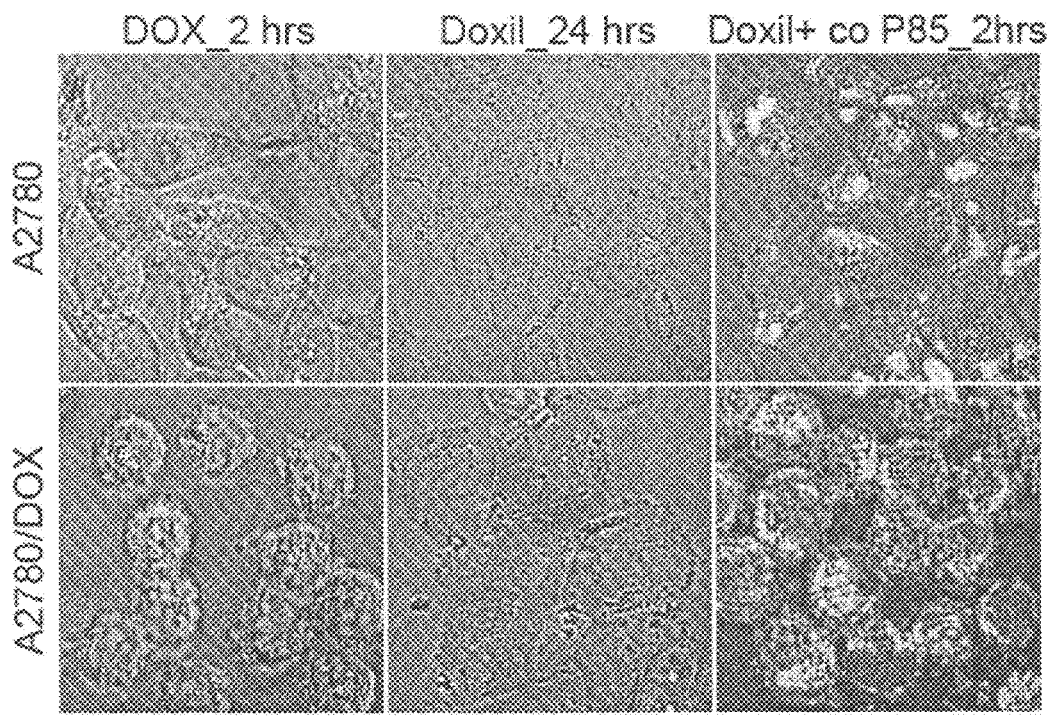
Figure 3B:
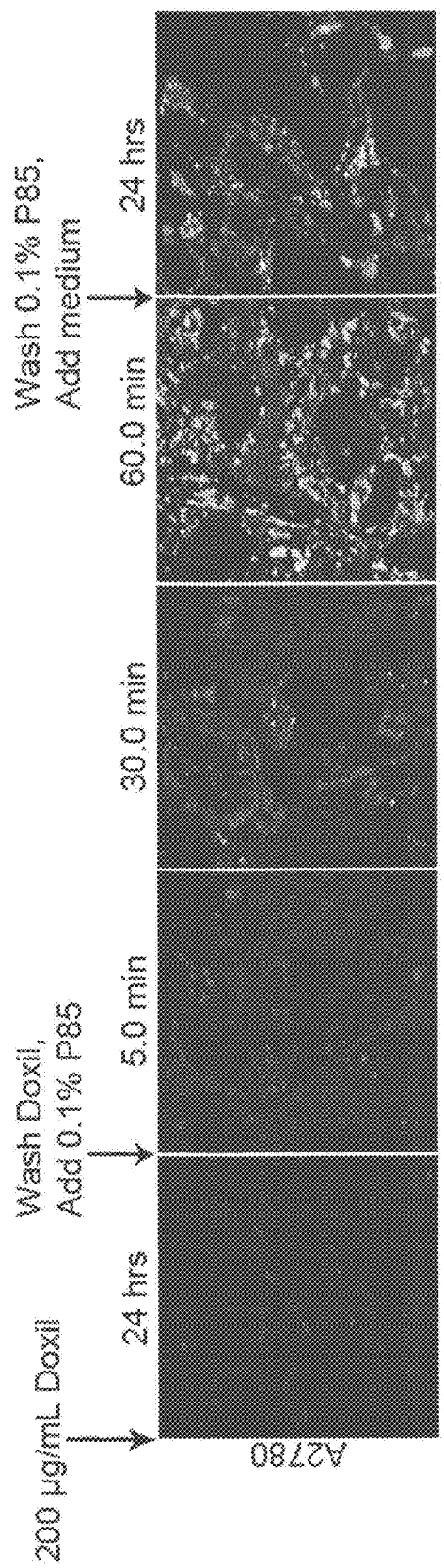
Figure 3C:
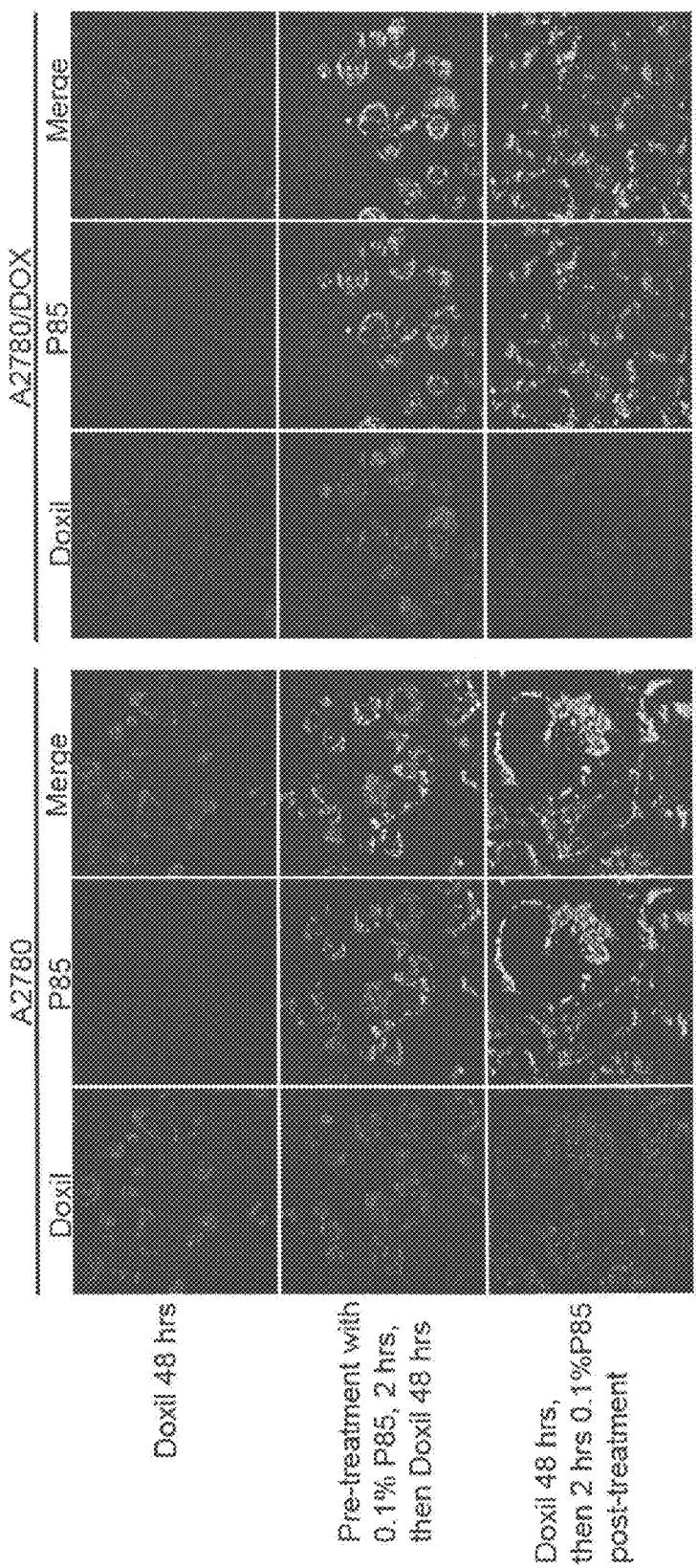

FIG. 3 provides confocal images of DOX localization in breast and ovarian cancer cell lines in the presence or absence of Pluronic® P85. FIG. 3A shows Doxil® uptake in A2780 and A2780/DOX cells after 2 or 24 hours incubation, in the presence of 0.1% Pluronic® P85, Doxil® uptake in A2780 and A2780/DOX cells after 2 hours incubation. Pluronic® P85 was labeled with Atto 647. FIG. 3B provides a time series imaging of post-treatment of A2780 cells with 0.1% Pluronic® P85 after 24 hours treatment with 200 μg/ml Doxil®. FIG. 3C shows the Doxil®/DOX uptake in A2780 and A2780/DOX cells at different treatment regimens with 0.1% P85. The last panels in each row present digitally superimposed images of two preceding panels to visualize the colocalization. Magnification 63×.

Figure 4:
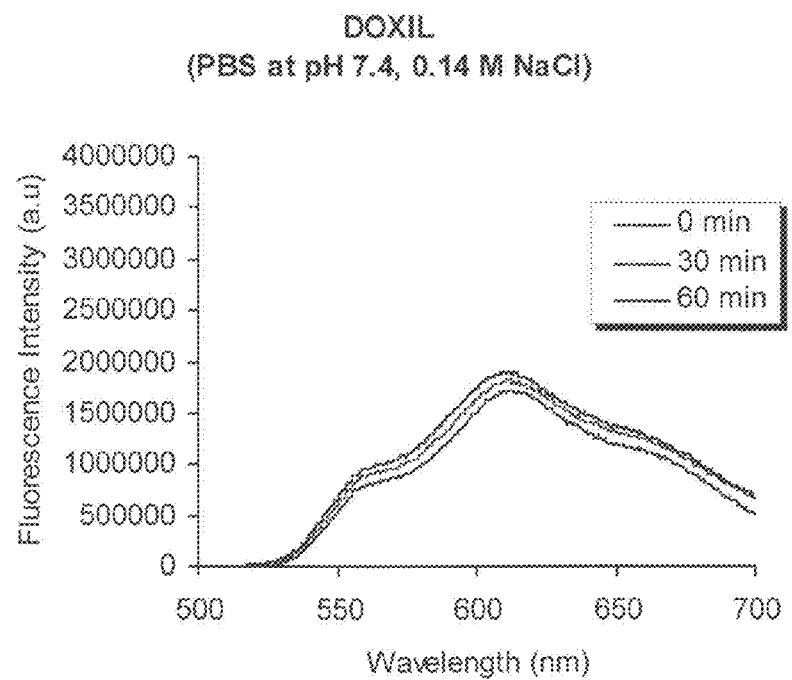
Figure 4:
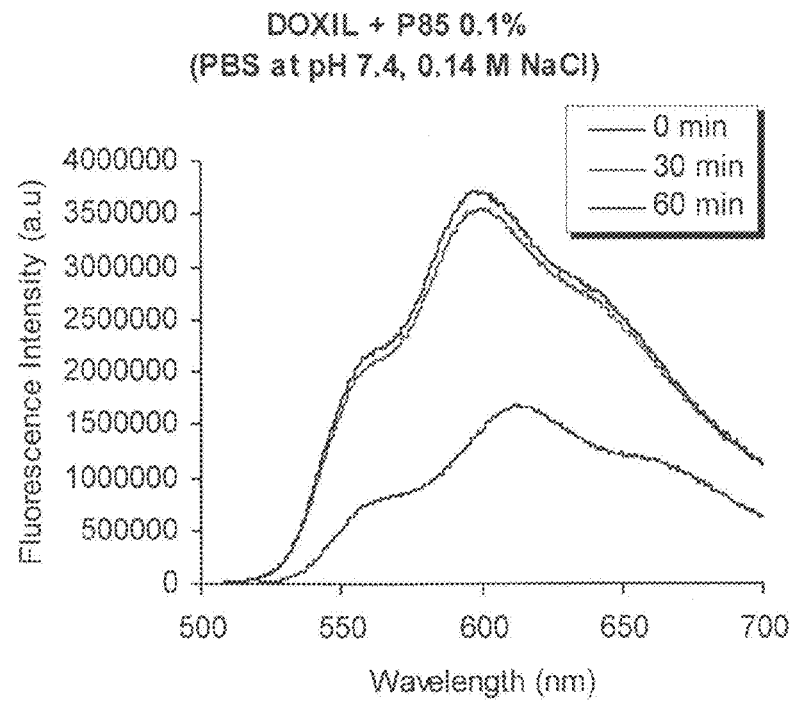

FIG. 4 provides the fluorescence spectra of free DOX and Doxil® liposome in the absence (FIG. 4A) or presence (FIG. 4B) of 0.1% Pluronic® P85.

Figure 5:
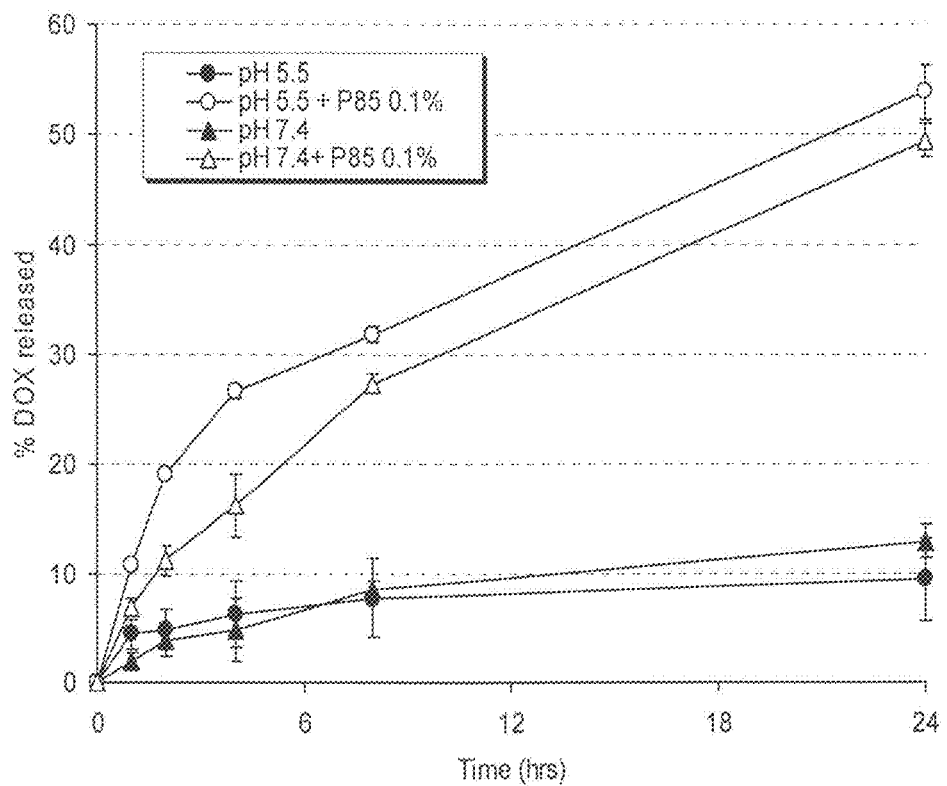

FIG. 5 provides the in vitro release profile of DOX from Doxil® mediated by P85 at 37° C. (●) pH5.5; (○) pH5.5 in 0.1% P85; (▲) pH7.4; (Δ) pH7.4 in 0.1% P85. Data are mean±SEM (n=4).

Figure 6:
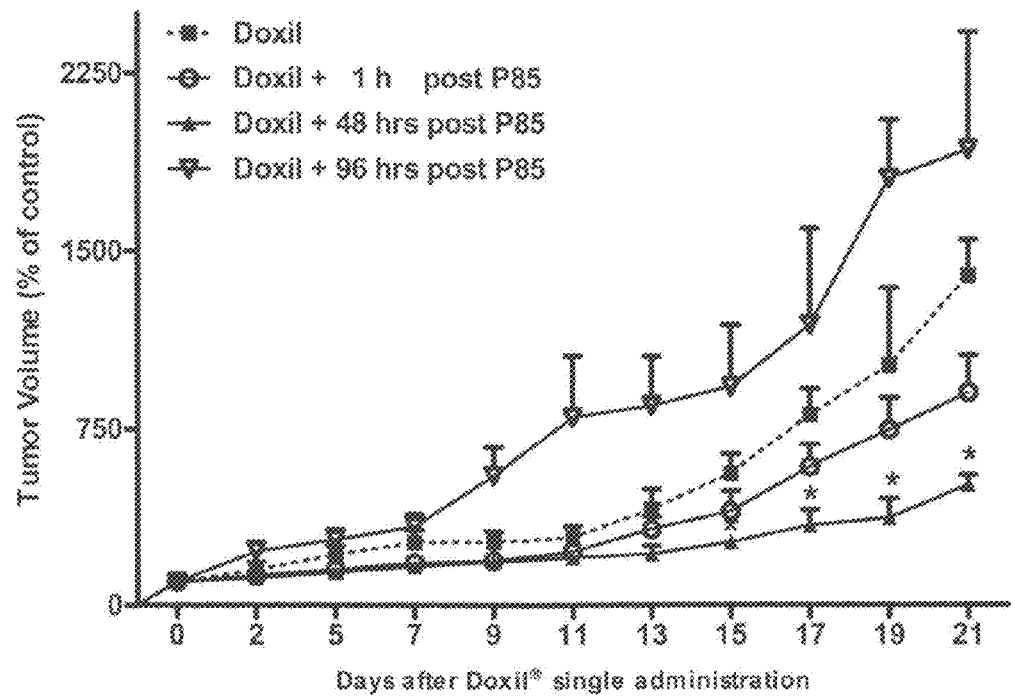

FIG. 6 shows the effect of Pluronic® P85 on tumor volume in the A2780 xenografts. Doxil® alone (■), Doxil® with 1 hour post treatment of 0.02% Pluronic® P85 (○), Doxil® with 48 hours post treatment of 0.02% Pluronic® P85 (▲), Doxil® with 96 hours post treatment of 0.02% Pluronic® P85 ( ). Treatment consisted of a single i.v. injection of 12 mg/kg of Doxil® given 2 weeks after tumor implantation. The data represent mean±SEM (n=8), * p<0.05. The p values were obtained using 2 ways ANOVA by comparing tumor volume in Doxil® group and other groups.

Figure 7:
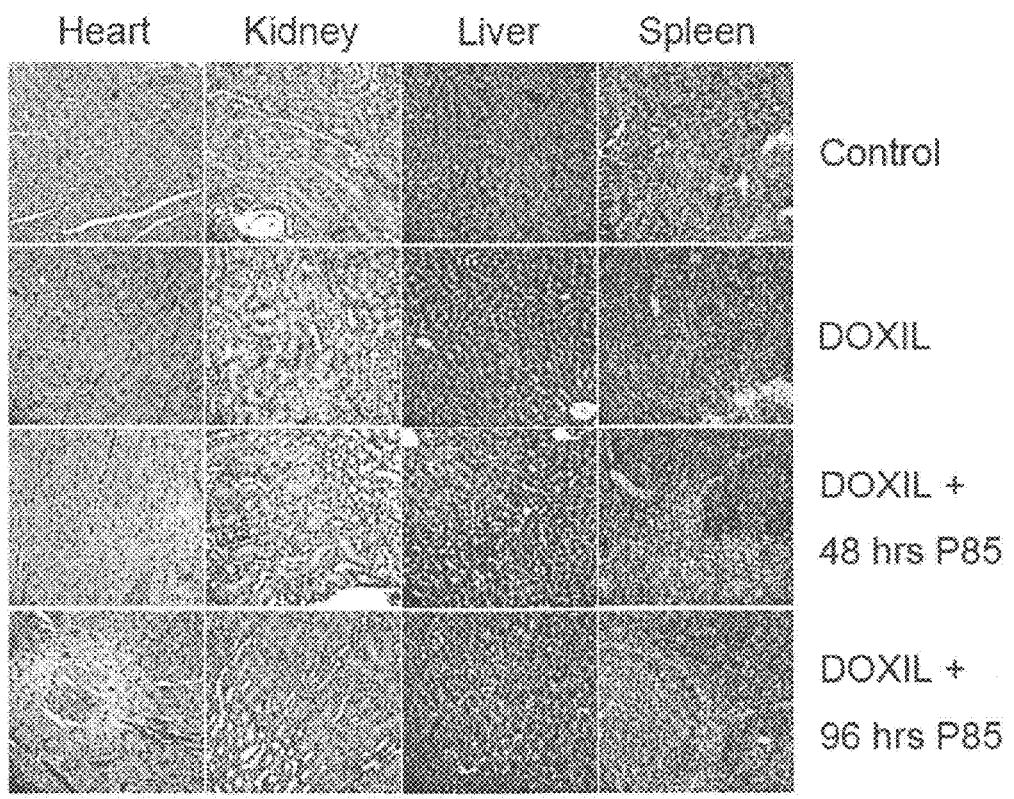

FIG. 7 provides H&E staining of heart, liver, spleen and kidney tissues from animals in 4 treatment groups: control, Doxil®, Doxil®+P85 48 hours later, Doxil®+P85 96 hours later.

Figure 8A:
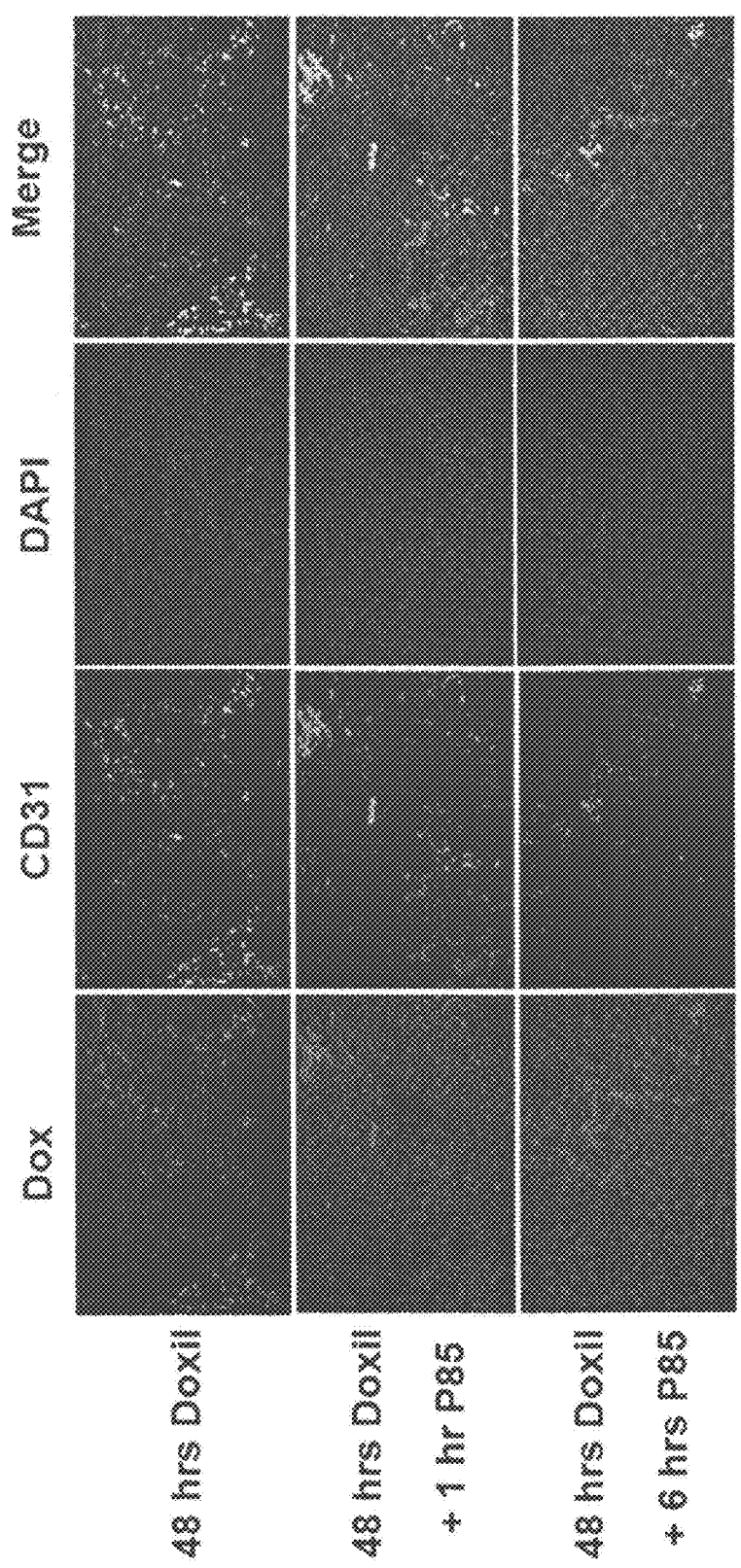
Figure 8:
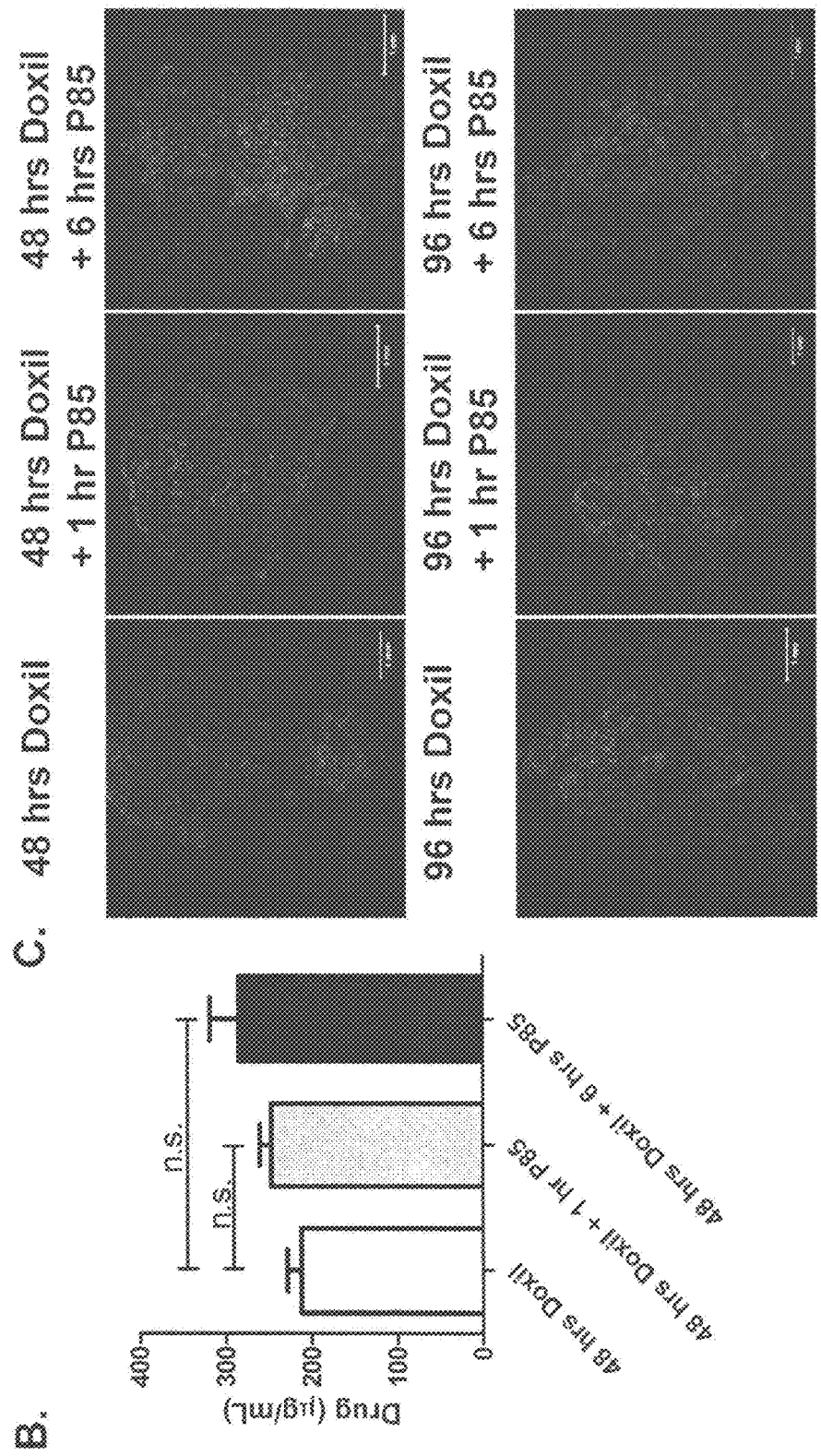

FIG. 8 shows the effect of P85 on anti-tumor efficacy and drug distribution in A2780 xenografts. Two weeks after tumor implantation, mice were treated by a single i.v. injection of 12 mg/kg of Doxil®. P85 (0.02%) was administered i.v. either 48 hours or 96 hours after the drug, animals were sacrificed, and tumor samples were collected 1 or 6 hours later. FIG. 8A provides fluorescent micrographs (×10) of distribution of drug in tumor sections stained for CD31 and nucleus. FIG. 8B provides an HPLC analysis of Dox in the tumor homogenates of tumors presented in FIG. 8A. Data are mean±SEM (n=5), *p<0.05, n.s.—no significance (unpaired t test with Welch's correction). FIG. 8C provides confocal images (×10) of drug distribution in tumor sections.

Figure 9:
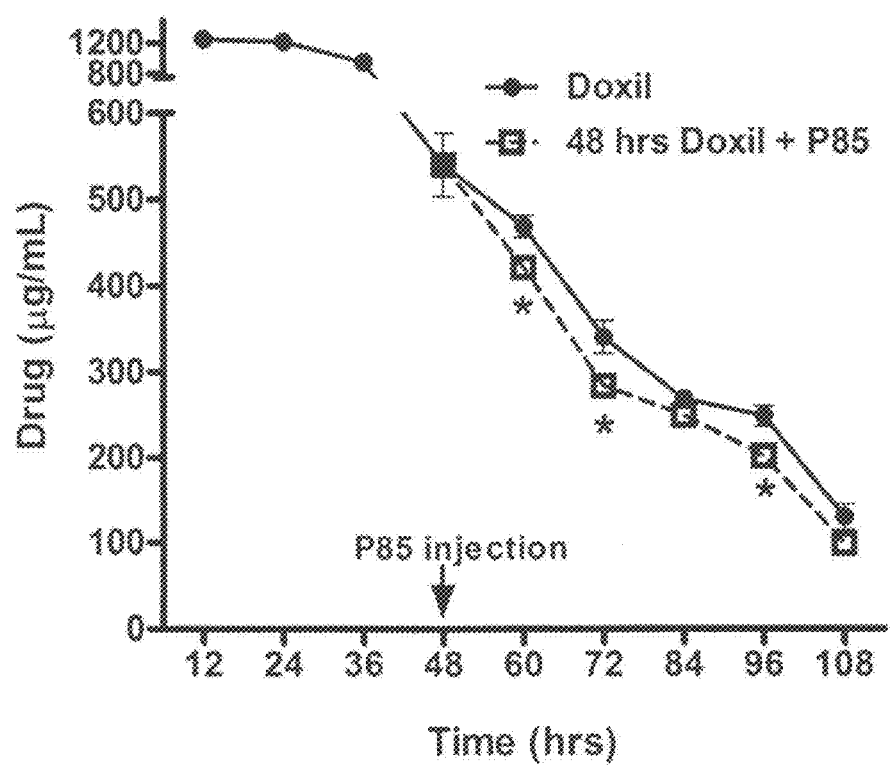

FIG. 9 provides an HPLC analysis of the effect of P85 on the plasma drug levels in the BALB/c mice. Mice were treated with a single i.v. injection of 12 mg/kg of Doxil®. P85 (0.02%, 100 µL/mice) was administered i.v. 48 hours after the drug, animals were sacrificed, and blood samples were collected every 12 hours after the treatments, followed by the HPLC analysis. Data are mean±SEM (n=5). * p<0.05 (unpaired t test with Welch's correction).

Figure 10:
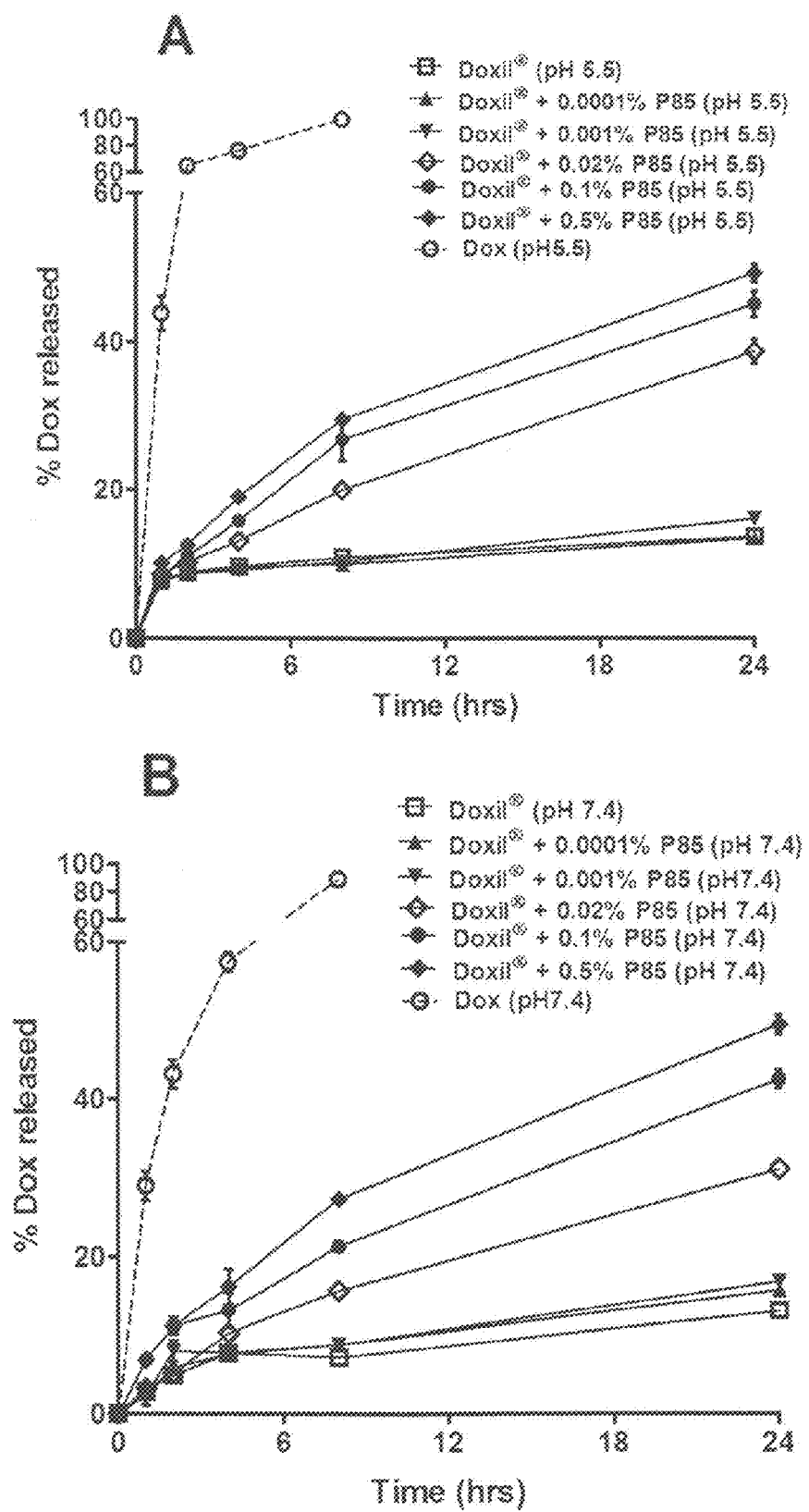
Figure 10:
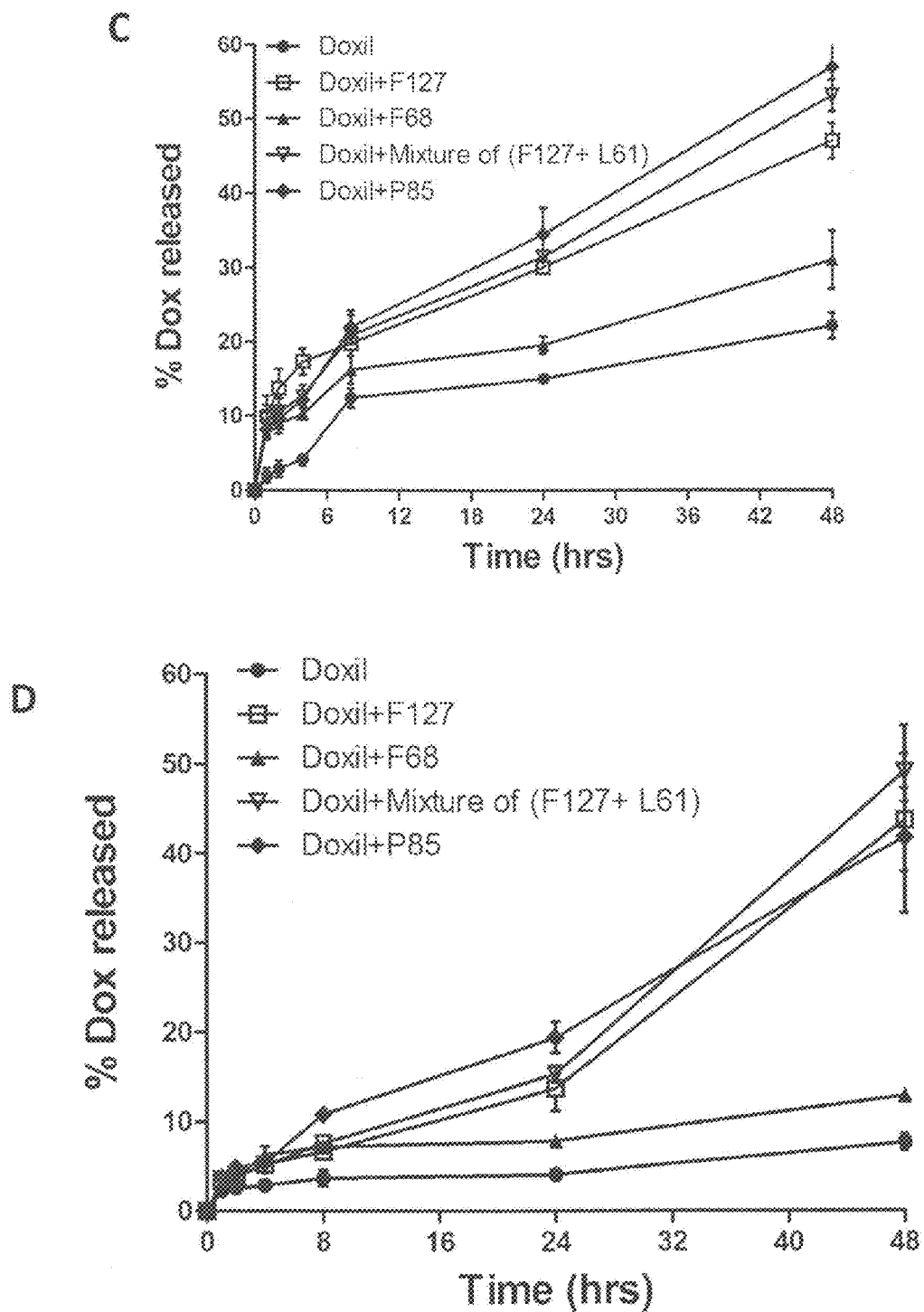

FIG. 10 shows the release of Dox from Doxil® liposomes triggered by Pluronics®. FIGS. 10A and 10B show Doxil® dispersed at 37° C. in either acetate buffer (pH 5.5; FIG. 10A) or PBS (pH 7.4; FIG. 10B) with or without P85. The concentration of Doxil® in the dispersion is 0.2 mg/mL. The concentration of P85 in the dispersion was 0.0001%, 0.001%, 0.02%, 0.1%, or 0.5%. The release of the free Dox (dashed line) from the dialysis bag is shown for comparison. FIGS. 10C and 10D show Doxil® dispersed at 37° C. in acetate buffer solution (pH5.5, FIG. 10C) or PBS (pH7.4, FIG. 10D) with or without 0.02% Pluronic® copolymers. Data are mean±SD (n=6).

Figure 11:
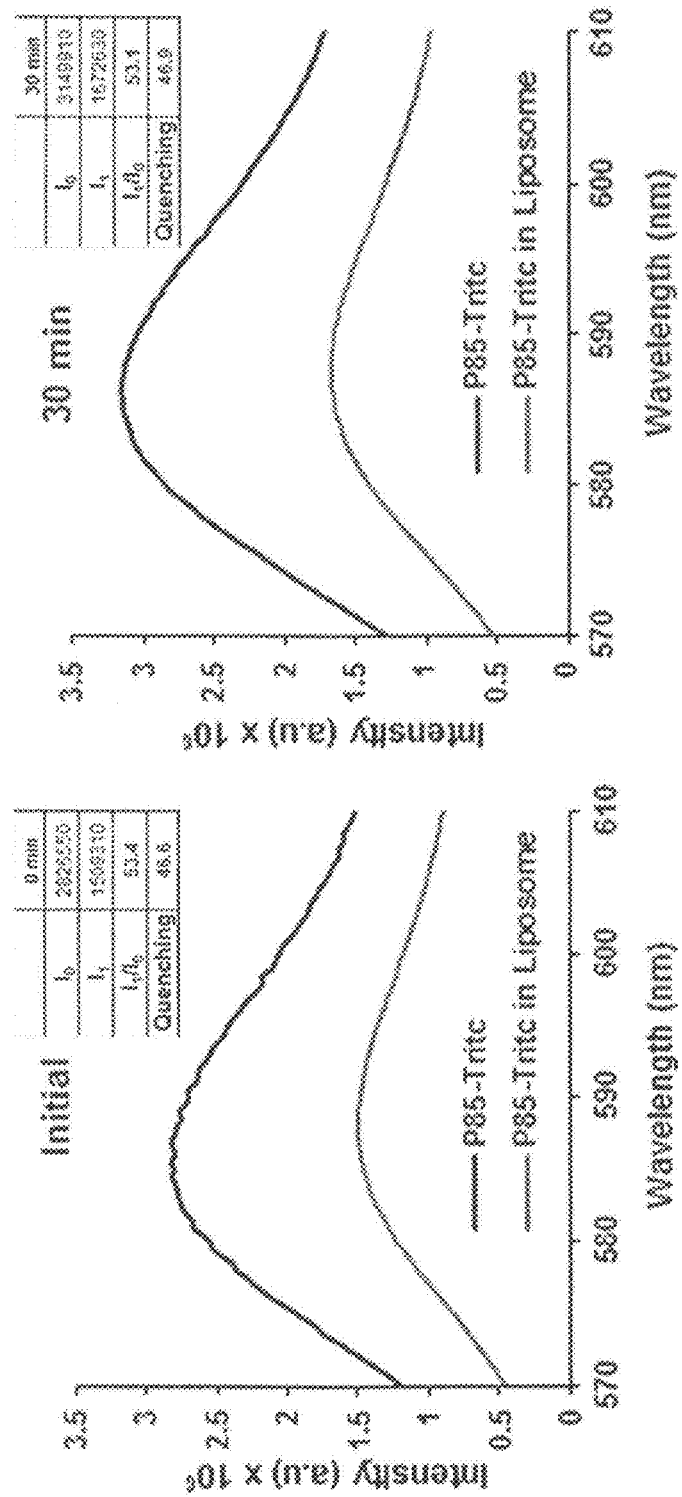

FIG. 11 provides fluorescence emission spectra of Tritc-P85 in the absence (top) or presence (bottom) of plain liposomes. The final concentration of the P85 in PBS (pH 7.4) was 0.1%. The plain liposomes have the same lipid composition as Doxil® (N-(carbonyl-methoxypolyethyleneglycol 2000)-1,2-distearoyl-sn-glycero-3-phosphoethanolamine sodium salt (MPEG-DSPE), 3.19 mg/mL; fully hydrogenated soy phosphatidylcholine (HSPC), 9.58 mg/mL; cholesterol, 3.19 mg/mL; ammonium sulfate, approximately 2 mg/mL; purchased from Encapsula NanoSciences Corp., Nashville, Tenn.). The final concentration of lipid used in the dispersion is ca. 0.232 mg/mL. The fluorescence emission spectra were recorded using a Fluorolog® (Horiba Jobin Yvon Inc., NJ) at $\lambda_{ex}$=550 nm with the bandwidth of 2 nm for excitation and emission. $I_0$ and $I_1$ are the maximum fluorescence intensities of Tritc-P85 without and with the liposomes.

DETAILED DESCRIPTION OF THE INVENTION

Liposomal drug delivery systems have been instrumental in developing the first generation of nanomedicines. These have already reached clinical stage providing a considerable benefit to patients, such as Doxil®, a liposomal form of doxorubicin (Dox) for the treatment of cancer, such as ovarian cancer (Song et al. (2012) J. Liposome Res., 22:177-92; Schwendener, R. A. (2007) Adv. Exp. Med. Biol., 620:117-128; Maurer et al. (2001) Expert Opin. Biol. Ther., 1:923-947; Torchilin, V. P. (2005) Nat. Rev. Drug Discov., 4:145-160). After systemic injection the Doxil® liposomes drain through the leaky tumor blood vessels and retain at the tumor sites, resulting in increased tumor accumulation of the liposomal drug compared to the free Dox. This general phenomenon is often referred to as "Enhanced Permeability and Retention" effect (EPR) (Maeda et al. (2001) J. Control Release, 74:47-61). However, further penetration of liposomal drug from the vascular regions to the distal tumor cells is hindered (Kostarelos et al. (2004) Int. J. Cancer, 112:713-721; Chauhan et al. (2011) Annu. Rev. Chem. Biomol. Eng., 2:281-298), particularly in the case of fibrotic tumors (Torchilin, V. P. (2005) Nat. Rev. Drug Discov., 4:145-160; Yuan et al. (1994) Cancer Res., 54:3352-3356). The latter produce viscoelastic gel-like extracellular matrix (ECM) that is rich in fibronectin and collagen, and is associated with poor survival (Kalluri et al. (2006) Nat. Rev. Cancer, 6:392-401; Bhowmick et al. (2004) Nature, 432: 332-337). Thus, methods that are able to improve the permeability of the matrix, for example collagen synthesis inhibitors, collagenase and hyaluronidase, or tumor-penetrating peptides have been used to facilitate the distribution and enhance the efficacy of liposomal drugs (Diop-Frimpong et al. (2011) Proc. Natl. Acad. Sci., 108:2909-2914; Eikenes et al. (2010) Anticancer Res., 30:359-368; Sugahara et al. (2010) Science 328:1031-1035; Jain et al. (2010) Nat. Rev. Clin. Oncol., 7:653-664). However, these methods lead to increased toxicity of the drug to normal tissues and/or enhance the risk of the tumor progression and metastasis (Diop-Frimpong et al. (2011) Proc. Natl. Acad. Sci., 108: 2909-2914). Other studies have also explored impacts of physical fields such as ultrasound, temperature (hyperthermia), or high energy radiation to enhance permeability of tumor microvasculature and/or microenviroment (Schroeder et al. (2009) J. Control Release, 137:63-68; Kong et al. (2000) Cancer Res., 60:6950-6957; Hagtvet et al. (2011) Radiat. Oncol., 6:135; Harrington et al. (2000) Clin. Cancer Res., 6:4939-4949; Khaibullina et al. (2008) J. Nucl. Med., 49:295-302). However, these methods are technically complex, and have limited use for distal and diffuse tumor sites. Moreover, several studies indicate that the cellular uptake of the intact liposome is restricted at the tumor site and the drug trapped in liposomes in interstitial space remains inactive until it is released in the free form (Barenholz et al. (2012) J. Control Release, 160:117-34; Zamboni, W. C. (2008) Oncologist, 13:248-260; Zamboni, W. C. (2005) Clin. Cancer Res., 11:8230-8234). Therefore, it would be ideal to enable the liposomes to release their low molecular weight cargo at the right site and the right time once the liposomal drug accumulates in the tumor vessels. This would allow for diffusion of the low molecular mass drug from the vascular sites into the distal tumor areas and could boost the cytotoxic effect of the drug upon the cancer cells. Thus, the strategies that could facilitate drug delivery to tumors followed with efficient release of the drug at the tumor sites with minimum side effects are urgently needed (Kwon et al. (2012) J. Control Release, 164:108-114; Bae et al. (2011) J. Control Release, 153:198-205; Florence, A. T. (2012) J. Control Release, 161:399-402). Here, a new simple strategy to promote the drug release from the liposomal carriers at the tumor sites is provided. This strategy employs the use of amphiphilic block copolymers (e.g., poly(ethylene oxide)-b-poly(propylene oxide)-b-poly(ethylene oxide), PEO-PPO-PEO) to facilitate drug delivery. Notably, this approach can be used with already approved liposomal drugs, such as Doxil®.

As stated hereinabove, DOXIL® is a PEGylated liposomal formulation of the small molecule drug doxorubicin. In a particular embodiment, DOXIL® contains 2 mg/ml of doxorubicin, 3.19 mg/ml of N-carbonylmethoxy polyethyleneglycol 2000-1,2-distearoyl-sn-glycero-3-phosphoethanolaminesodium salt (DSPE-PEG 2000), 9.58 mg/ml of fully hydrogenated soy phosphatidylcholine, and 3.19 mg/ml of cholesterol. DOXIL® has been extensively used in clinics for the treatment of various types of cancers, but has had only limited efficacy in these therapies for the reasons set forth above.

Herein, it is shown that administering amphiphilic copolymers, such as those comprising polyoxyethylene and polyoxypropylene blocks, with liposomal doxorubicin results in substantially higher cytotoxicity of doxorubicin than in the absence of the amphiphilic block copolymer. For example, the data provided herewith shows that treatment of breast cancer cell lines MCF7, MCF7/MX and MCF7/ADR with amphiphilic block copolymer and liposomal doxorubicin is cytotoxic. However, the treatment with the liposomal doxorubicin alone was not cytotoxic at the concentrations used in the experiment when added to culture for 2 hours. Without being bound by theory, the increased cytotoxicity may be explained by significantly higher uptake of the liposomal doxorubicin into the cells in the presence of or after pretreatment with the amphiphilic block copolymer.

It is also demonstrated herein that doxorubicin release out of liposomes is stimulated when cultures were exposed to the amphiphilic block copolymer, e.g., when pretreated with the amphiphilic block copolymer or when the amphiphilic block copolymer was administered to cultures with or after liposomal doxorubicin.

The effect of amphiphilic block copolymer administration on intracellular trafficking and uptake of liposomal doxorubicin in breast cancer cells was also evaluated. The treatment of the breast cancer cells with liposomal doxorubicin alone resulted in uptake and localization of the drug in the intracellular vesicles. When cells were treated with the liposomal doxorubicin in the presence of 0.1% amphiphilic block copolymer, the nuclear uptake of the drug was observed as early as after 15 minutes and, after 60 minutes, most of the drug was localized in the nucleus.

The instant invention encompasses methods of increasing the efficacy of an encapsulated compound (e.g., therapeutic agent or diagnostic agent) by co-administering (e.g., prior, during, and/or after) at least one amphiphilic block copolymer. The instant invention also encompasses methods of increasing the delivery of an encapsulated compound (e.g., therapeutic agent or diagnostic agent) to the nucleus of cell by co-administering (e.g., prior, during, and/or after) at least one amphiphilic block copolymer. The therapeutic agent may be encapsulated in a micelle or liposome, particularly a liposome. In a particular embodiment, the therapeutic agent acts in the nucleus (i.e., the therapeutic agent is delivered to the nucleus to exert its therapeutic effect). In a particular embodiment, the therapeutic agent is a chemotherapeutic agent. Particularly, the chemotherapeutic agent is a DNA damaging agent (see below), particularly a DNA intercalater such as an anthracycline. In a particular embodiment, the chemotherapeutic agent is doxorubicin.

The encapsulated compound may be any bioactive agent such as a therapeutic agent or diagnostic agent. The compound may also be a test compound to be screened as potential leads in the development of therapeutic agents. Encapsulated compounds include, without limitation, polypeptides, peptides, glycoproteins, nucleic acids, synthetic and natural drugs, peptoides, polyenes, macrocyles, glycosides, terpenes, terpenoids, aliphatic and aromatic compounds, small molecules, and their derivatives and salts. In a particular embodiment, the encapsulated compound is a small molecule.

Liposomal formulations have been developed for numerous anticancer drugs over the years that are currently in different stages of clinical development. Examples include but not limited to liposomal doxorubicin (Doxil®, Caelyx®, Myocet®), liposomal daunorubicin (DaunoXome®), PEGylated liposomal cisplatin (SPI-077, Lipoplatin®, LiPlaCis®), liposomal encapsulated paclitaxel (LEP-ETU, PNU-93914), liposomal vincristine (OncoTCS®), liposomal mitoxantrone (MEM) and others. Liposomal formulations of anticancer drugs are often associated with improved toxicity profiles and better antitumor activities, however further optimization is needed to improve efficiency of the formulations. Combination therapies of liposomal formulations with other anticancer drugs have shown promising results in various clinical trials (Hofheinz et al. (2005) Anti-Cancer Drugs, 16:691-707). As shown herein, amphiphilic block copolymers, particularly triblock copolymers such as poloxamers or Pluronics® consisting of polyoxyethylene-polyoxypropylene-polyoxyethylene, can be used in combination with these therapies to facilitate the release of the drug at the tumor site. For example, the method may comprise 1) pretreatment with the amphiphilic block copolymer followed by administration of liposomal formulation of anticancer drug; 2) simultaneous administration of the amphiphilic block copolymer and liposomal formulation of anticancer drug; and/or 3) treatment with liposomal formulation of anticancer drug with consequent post-treatment with the amphiphilic block copolymer. In a particular embodiment, the liposomal drug formulation is administered to the patient first and then the amphiphilic block copolymer is subsequently administered to the patient after the liposomal drug formulation. Cancer type can be chosen based on primary application of the liposomal anticancer drug formulation.

While any type of compound may be delivered to a cell or subject by the compositions and methods of the instant invention, the following description of the inventions exemplifies the compound as a therapeutic agent, particularly doxorubicin, for simplicity.

In a particular embodiment of the invention, the amphiphilic block copolymer is a copolymer comprising at least one block of poly(oxyethylene) and at least one block of poly(oxypropylene). Amphiphilic block copolymers are exemplified by the block copolymers having the formulas:

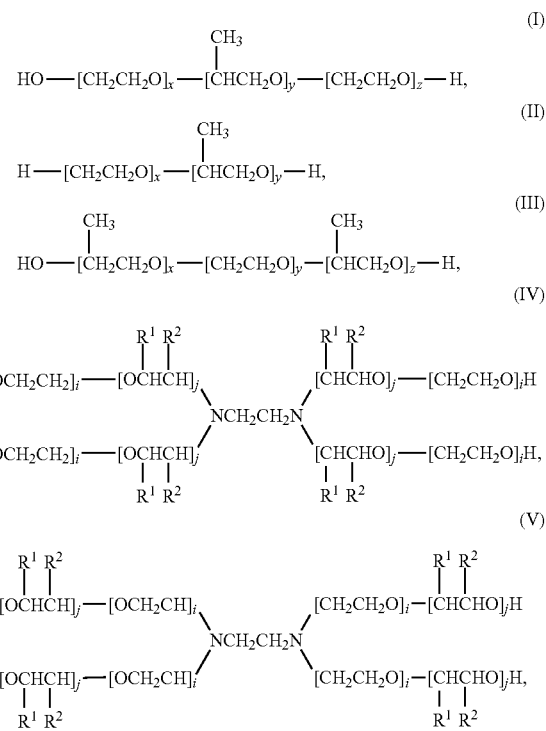

in which x, y, z, i, and j have values from about 2 to about 800, preferably from about 5 to about 200, more preferably from about 5 to about 80, and wherein for each $R^1$, $R^2$ pair, as shown in formula (IV) and (V), one is hydrogen and the other is a methyl group. The ordinarily skilled artisan will recognize that the values of x, y, and z will usually represent a statistical average and that the values of x and z are often, though not necessarily, the same. Formulas (I) through (III) are oversimplified in that, in practice, the orientation of the isopropylene radicals within the B block will be random. This random orientation is indicated in formulas (IV) and (V), which are more complete. Such poly(oxyethylene)-poly (oxypropylene) compounds have been described by Santon (Am. Perfumer Cosmet. (1958) 72(4):54-58); Schmolka (Loc. cit. (1967) 82(7):25-30), Schick, ed. (Non-ionic Suifactants, Dekker, N.Y., 1967 pp. 300-371). A number of such compounds are commercially available under such generic trade names as "lipoloxamers", "Pluronic®," "poloxamers," and "synperonics." Pluronic® copolymers within the B-A-B formula, as opposed to the A-B-A formula typical of Pluronics®, are often referred to as "reversed" Pluronics®, "Pluronic® R" or "meroxapol." Generally, block copolymers can be described in terms of having hydrophilic "A" and hydrophobic "B" block segments. Thus, for example, a copolymer of the formula A-B-A is a triblock copolymer consisting of a hydrophilic block connected to a hydrophobic block connected to another hydrophilic block. The "polyoxamine" polymer of formula (IV) is available from BASF under the tradenameTetronic®. The order of the polyoxyethylene and polyoxypropylene blocks represented in formula (IV) can be reversed, creating Tetronic R®, also available from BASF (see, Schmolka, J. Am. Oil. Soc. (1979) 59:110).

Polyoxypropylene-polyoxyethylene block copolymers can also be designed with hydrophilic blocks comprising a random mix of ethylene oxide and propylene oxide repeating units. To maintain the hydrophilic character of the block, ethylene oxide can predominate. Similarly, the hydrophobic block can be a mixture of ethylene oxide and propylene oxide repeating units. Such block copolymers are available from BASF under the tradename Pluradot™. Poly(oxyethylene)-poly(oxypropylene) block units making up the first segment need not consist solely of ethylene oxide. Nor is it necessary that all of the B-type segment consist solely of propylene oxide units. Instead, in the simplest cases, for example, at least one of the monomers in segment A may be substituted with a side chain group.

A number of poloxamer copolymers are designed to meet the following formula:

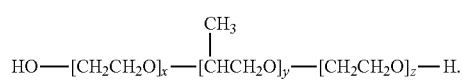

(I)

Examples of poloxamers include, without limitation, Pluronic® L31, L35, F38, L42, L43, L44, L61, L62, L63, L64, P65, F68, L72, P75, F77, L81, P84, P85, F87, F88, L92, F98, L101, P103, P104, P105, F108, L121, L122, L123, F127, 10R5, 10R8, 12R3, 17R1, 17R2, 17R4, 17R8, 22R4, 25R1, 25R2, 25R4, 25R5, 25R8, 31R1, 31R2, and 31R4. Pluronic® block copolymers are designated by a letter prefix followed by a two or a three digit number. The letter prefixes (L, P, or F) refer to the physical form of each polymer, (liquid, paste, or flakeable solid). The numeric code defines the structural parameters of the block copolymer. The last digit of this code approximates the weight content of EOblock in tens of weight percent (for example, 80% weight if the digit is 8, or 10% weight if the digit is 1). The remaining first one or two digits encode the molecular mass of the central PO block. To decipher the code, one should multiply the corresponding number by 300 to obtain the approximate molecular mass in daltons (Da). Therefore Pluronic nomenclature provides a convenient approach to estimate the characteristics of the block copolymer in the absence of reference literature. For example, the code 'F127' defines the block copolymer, which is a solid, has a PO block of 3600 Da (12×300) and 70% weight of EO. The precise molecular characteristics of each Pluronic® block copolymer can be obtained from the manufacturer.

In a particular embodiment, the amphiphilic block copolymer is a PEO-PPO-PEO triblock copolymer. In a particular embodiment, the PEO-PPO-PEO triblock copolymer comprises about 15 to about 35, particularly about 20 to about 30 PEO monomers at each end and a center block of about 30 to about 50, particularly about 35 to about 45 PPO monomers. In one embodiment, the PEO/PPO/PEO monomer unit ratio is 26/40/26. In a particular embodiment, the amphiphilic block copolymer is poloxamer 235.

The amphiphilic block copolymers may have a PPO content of at least 30% wt, at least 40% wt, or at least 50% wt. The amphiphilic block copolymers may have a PPO block molecular mass of at least about 1200 or 1700 to about 3000, 3600, or 4200. In a particular embodiment, the amphiphilic block copolymer is a PEO-PPO-PEO triblock copolymer with a PPO content of at least 30% wt and a PPO block molecular mass from about 1200 to about 4200; a PPO content of at least 40% wt and a PPO block molecular mass from about 1700 to about 3600; or, more particularly, a PPO content of at least 50% wt and a PPO block molecular mass from about 1700 to about 3000. In a particular embodiment, the amphiphilic block copolymer has a hydrophilic-lipophilic balance (HLB) of about 22 or less. In a particular embodiment, the amphiphilic block copolymer has a critical micelle concentration (CMC) of about 0.4 mM or less, particularly about 0.1 mM or less.

As stated hereinabove, more than one block copolymer may be used. In other words, a mixture or blend of block copolymers may be used. For example, the mixture or blend may comprise at least one PEO-PPO-PEO triblock copolymer. For example, the mixture may comprise at least one first amphiphilic block copolymer and at least one second amphiphilic block copolymer. In a particular embodiment, (1) the first amphiphilic block copolymer is a PEO-PPO-PEO triblock copolymer with a PPO content of at least 30% and the second amphiphilic block copolymer is PEO-PPO-PEO triblock copolymer with a PPO content of 70% or less; (2) the first amphiphilic block copolymer is a PEO-PPO-PEO triblock copolymer with a PPO content of at least 40% and the second amphiphilic block copolymer is a PEO-PPO-PEO triblock copolymer with a PPO content of 60% or less; (3) the first amphiphilic block copolymer is a PEO-PPO-PEO triblock copolymer with a PPO content of at least 50% and the second amphiphilic block copolymer is a PEO-PPO-PEO triblock copolymer with a PPO content of 50% or less; (4) the first amphiphilic block copolymer is a PEO-PPO-PEO triblock copolymer with a PPO content of at least 60% and the second amphiphilic block copolymer is a PEO-PPO-PEO triblock copolymer with a PPO content of 40% or less; or (5) the first amphiphilic block copolymer is a one PEO-PPO-PEO triblock copolymer with a PPO content of at least 70% and the second amphiphilic block copolymer is a PEO-PPO-PEO triblock copolymer with a PPO content of 30% or less. In the case of mixtures, the PEO-PPO-PEO block copolymers, independently of each other, may have a PPO block molecular mass from about 900 to about 4200, from about 1700 to about 3600, or, more particularly, from about 1700 to about 3000. The block copolymers may be present in any ratio (e.g., from about 1:1 to about 1:10 or more).

Administration

The instant invention encompasses compositions comprising at least one amphiphilic block copolymer, at least one encapsulated therapeutic agent (e.g., liposomal doxorubicin), and at least one pharmaceutically acceptable carrier. The instant invention also encompasses comprising a first composition comprising at least one amphiphilic block copolymer and at least one pharmaceutically acceptable carrier and a second composition comprising at least one encapsulated therapeutic agent and at least one therapeutic agent. The compositions of the instant invention may further comprise other therapeutic agents (e.g., other chemotherapeutic agents).

The present invention also encompasses methods for preventing, inhibiting, and/or treating a disease or disorder (e.g., a cancer/neoplasia) in a subject. The methods comprise administering at least one amphiphilic block copolymer and at least one encapsulated therapeutic agent (related to the disease or disorder) to the subject. The pharmaceutical composition(s) of the instant invention can be administered to an animal, in particular a mammal, more particularly a human, in order to treat/inhibit cancer. The amphiphilic block copolymer may be administered in the same composition as the encapsulated therapeutic agent or in different compositions. The amphiphilic block copolymer may be administered concurrently and/or sequentially with the encapsulated therapeutic agent. For example, the amphiphilic block copolymer may be administered to the subject prior to the administration of the encapsulated therapeutic agent, may be co-administered with the encapsulated therapeutic agent, and/or may be administered after the administration of the encapsulated therapeutic agent.

In a particular embodiment, the amphiphilic block copolymer is administered after the encapsulated therapeutic agent (e.g., liposomal doxorubicin). The amphiphilic block copolymer may be administered after sufficient time to ensure disposition (e.g., the greatest amount) of the encapsulated therapeutic agent to the target site (e.g., tumor). The time point of the maximal accumulation ($t_{max}$ [hrs]) of Doxil® in tumor models after single injections has been described (Penate Medina et al. (2011) J. Drug Deliv., 2011:160515; Laginha et al. (2005) Clin. Cancer Res., 11:6944-6949; Charrois et al. (2003) J. Pharmacol. Exp. Ther., 306:1058-1067; Vaage et al. (1997) Br. J. Cancer, 75:482-486). In a particular embodiment, the amphiphilic block copolymer is administered within 96 hours, within 72 hours, within 48 hours, within 24 hours, within 12 hours, within 6 hours, within 4 hours, within 2 hours, within 1 hour, within 0.5 hour, or less after the administration of the encapsulated therapeutic. In a particular embodiment, the amphiphilic block copolymer is administered about 1 hour to about 48 hours, particularly 24 hours after administration of the encapsulated therapeutic.

The amphiphilic block copolymer may be present in the composition at any concentration. In a particular embodiment, the amphiphilic block copolymer is present at a concentration from about 0.001% to about 5%. In a particular embodiment, the concentration of the amphiphilic block copolymer is from about 0.01% to about 2% or about 0.05% to about 2%.

In a particular embodiment, the therapeutic agent is a chemotherapeutic agent. The term "chemotherapeutic agent" means anti-cancer and other anti-hyperproliferative agents. Chemotherapeutic agents are compounds that exhibit anticancer activity and/or are detrimental to a cell. Chemotherapeutic agents include, without limitation: (1) DNA damaging agents (e.g., agents that inhibit DNA synthesis): anthracyclines (e.g., doxorubicin, daunorubicin, epirubicin), alkylating agents (e.g., nitrogen mustards, bendamustine, altretamine, methanesulphonateesters, busulfan, carboplatin, nitrosoureas, carmustine, cisplatin, chlorambucil, cyclophosphamide, dacarbazine, hexamethylmelamine, isofamide, ifosfamide, lomustine, mechlorethamine, alkyl sulfonates, epirubicin, idarubicin, triazines, ethylenimines, melphalan, mitotane, mytomycin, pipobroman, procarbazine, streptozocin, aziridines, thiotepa, uracil mustard, and triethylenemelamine), platinum derivatives (e.g., cisplatin, carboplatin, tetraplatin, ormaplatin, thioplatin, satraplatin, nedaplatin, oxaliplatin, heptaplatin, iproplatin, transplatin, lobaplatin, and cisdiamminedichloroplatinum), telomerase and topoisomerase inhibitors (e.g., topotecan, irinotecan, etoposide, teniposide, amsacrine, menogaril, amonafide, dactinomycin, daunorubicin, N,N-dibenzyldaunomycin, ellipticine, daunomycin, pyrazoloacridine, idarubicin, mitoxantrone, m-ANSA, doxorubicin, deoxyrubicin, oxanthrazole, rubidazone, epirubicin, and bleomycin), DNA minor groove binding agents (e.g., plicamydin); (2) tubulin interactive agents (e.g., vincristine, vinblastine, paclitaxel, taxoids, paclitaxel, docetaxel, and BAY 59-8862); (3) antimetabolites such as capecitabine, chlorodeoxyadenosine, cytarabine, ara-CMP, cytosine arabinoside, asparginase, azacitidine, dacabazine, floxuridine, fludarabine, 5-fluorouracil, 5-DFUR, gemcitibine, hydroxyurea, 6-mercaptopurine, methotrexate, pentostatin, pemetrexed, trimetrexate, and 6-thioguanine; (4) anti-angiogenics (e.g., Avastin®, thalidomide, sunitinib, lenalidomide) and vascular disrupting agents (e.g., flavonoids/flavones, DMXAA, combretastatin derivatives such as CA4DP, ZD6126, AVE8062A); (5) antibodies or antibody fragments (e.g., trastuzumab, bevacizumab, rituximab, ibritumomab, gemtuzumab, alemtuzumab, cetuximab, ranibizumab); and (6) hormonal agents/endocrine therapy: aromatase inhibitors (e.g., 4-hydroandrostendione, exemestane, aminoglutehimide, anastrozole, letozole), anti-estrogens (e.g., Tamoxifen, Toremifine, Raoxifene, Faslodex), anti-androgen agents (e.g., flutamide), anti-adrenal agents (e.g., mitotane and aminoglutethimide), and steroids (e.g., adrenal corticosteroids, prednisone, dexamethasone, methylprednisolone, and prednisolone); and (7) anti-mitotic compounds such as navelbine, epothilones, taxanes (e.g., paclitaxel, taxotere, docetaxel), vinca alkaloids, estramustine, vinblastine, vincristine, vindesine, and vinorelbine).

Cancers that may be treated using the present protocol include, but are not limited to: cancers of the prostate, colorectum, pancreas, cervix, stomach, endometrium, brain, liver, bladder, ovary, testis, head, neck, skin (including melanoma and basal carcinoma), mesothelial lining, white blood cell (including lymphoma and leukemia) esophagus, breast, muscle, connective tissue, lung (including small-cell lung carcinoma and non-small-cell carcinoma), adrenal gland, thyroid, kidney, or bone; glioblastoma, mesothelioma, renal cell carcinoma, gastric carcinoma, sarcoma, choriocarcinoma, cutaneous basocellular carcinoma, skin squamous cell carcinomas, and testicular seminoma. In a particular embodiment, the cancer is selected from the group consisting of ovarian cancer, lung cancer including small-cell and non-small cell lung cancer, gastric cancer, breast cancer, Kaposi's sarcoma, uterine cancer, hematological cancer including multiple myeloma, lymphoma, Hodgkin's lymphoma and Non-Hodgkin's lymphoma and ovarian cancer.

The composition(s) described herein will generally be administered to a patient as a pharmaceutical preparation. The term "patient" as used herein refers to human or animal subjects. These compositions may be employed therapeutically, under the guidance of a physician.

The compositions of the instant invention may be conveniently formulated for administration with any pharmaceutically acceptable carrier(s). For example, the agents may be formulated with an acceptable medium such as water, buffered saline, ethanol, polyol (for example, glycerol, propylene glycol, liquid polyethylene glycol and the like), dimethyl sulfoxide (DMSO), oils, detergents, suspending agents or suitable mixtures thereof. The concentration of the agents in the chosen medium may be varied and the medium may be chosen based on the desired route of administration of the pharmaceutical preparation. Except insofar as any conventional media or agent is incompatible with the agents to be administered, its use in the pharmaceutical preparation is contemplated. Notably, formulations and dosages of liposomal doxorubicin (DOXIL®) are well known in the art (see, e.g., DOXIL® Product Information (2010) Centocor Ortho Biotec Products).

The dose and dosage regimen of compositions according to the invention that are suitable for administration to a particular patient may be determined by a physician considering the patient's age, sex, weight, general medical condition, and the specific condition for which the composition is being administered and the severity thereof. The physician may also take into account the route of administration, the pharmaceutical carrier, and the composition's biological activity.

Selection of a suitable pharmaceutical preparation will also depend upon the mode of administration chosen. For example, the compositions of the invention may be administered by direct injection to a desired site (e.g., a tumor). In this instance, a pharmaceutical preparation comprises the agents dispersed in a medium that is compatible with the site of injection. Compositions of the instant invention may be administered by any method. For example, the compositions of the instant invention can be administered, without limitation parenterally, subcutaneously, orally, topically, pulmonarily, rectally, vaginally, intravenously, intraperitoneally, intrathecally, intracerbrally, epidurally, intramuscularly, intradermally, or intracarotidly. In a particular embodiment, the compositions are administered by injection, such as intravenously or intraperitoneally. Pharmaceutical preparations for injection are known in the art. If injection is selected as a method for administering the composition, steps must be taken to ensure that sufficient amounts of the molecules reach their target cells to exert a biological effect.

Pharmaceutical compositions containing an agent of the present invention as the active ingredient in intimate admixture with a pharmaceutically acceptable carrier can be prepared according to conventional pharmaceutical compounding techniques. The carrier may take a wide variety of forms depending on the form of preparation desired for administration, e.g., intravenous or direct injection.

In a particular embodiment, the encapsulated therapeutic agent (e.g., liposomal doxorubicin) is administered via injection, particularly intravenous injection. In a particular embodiment, the amphiphilic block copolymer is administered via injection, e.g., intravenous, subcutaneous, or intramuscular.

A pharmaceutical preparation of the invention may be formulated in dosage unit form for ease of administration and uniformity of dosage. Dosage unit form, as used herein, refers to a physically discrete unit of the pharmaceutical preparation appropriate for the patient undergoing treatment. Each dosage should contain a quantity of active ingredient calculated to produce the desired effect in association with the selected pharmaceutical carrier. Procedures for determining the appropriate dosage unit are well known to those skilled in the art.

Dosage units may be proportionately increased or decreased based on the weight of the patient. Appropriate concentrations for alleviation of a particular pathological condition may be determined by dosage concentration curve calculations, as known in the art.

In accordance with the present invention, the appropriate dosage unit for the administration of compositions of the instant invention may be determined by evaluating the toxicity of the molecules or cells in animal models. Various concentrations of agents in pharmaceutical preparations may be administered to mice, and the minimal and maximal dosages may be determined based on the beneficial results and side effects observed as a result of the treatment. Appropriate dosage unit may also be determined by assessing the efficacy of the agent treatment in combination with other standard drugs. The dosage units of the compositions may be determined individually or in combination with each treatment according to the effect detected.

The pharmaceutical preparation comprising the agents of the instant invention may be administered at appropriate intervals, for example, at least twice a day or more until the pathological symptoms are reduced or alleviated, after which the dosage may be reduced to a maintenance level. The appropriate interval in a particular case would normally depend on the condition of the patient.

Other methods of treating cancer may be combined with the methods of the instant invention. For example, other chemotherapeutic agents may be administered (e.g., simultaneously and/or consecutively). Cancer therapies such as radiation and/or surgery (e.g., tumor excision) may also be co-administered with the compositions of the instant invention.

Definitions

The singular forms "a," "an," and "the" include plural referents unless the context clearly dictates otherwise.

"Pharmaceutically acceptable" indicates approval by a regulatory agency of the Federal or a state government or listed in the U.S. Pharmacopeia or other generally recognized pharmacopeia for use in animals, and more particularly in humans.

A "carrier" refers to, for example, a diluent, adjuvant, preservative (e.g., Thimersol, benzyl alcohol), anti-oxidant (e.g., ascorbic acid, sodium metabisulfite), solubilizer (e.g., Tween 80, Polysorbate 80), emulsifier, buffer (e.g., TrisHCl, acetate, phosphate), antimicrobial, bulking substance (e.g., lactose, mannitol), excipient, auxiliary agent or vehicle with which an active agent of the present invention is administered. Pharmaceutically acceptable carriers can be sterile liquids, such as water and oils, including those of petroleum, animal, vegetable or synthetic origin. Water or aqueous saline solutions and aqueous dextrose and glycerol solutions are preferably employed as carriers, particularly for injectable solutions. Suitable pharmaceutical carriers are described in "Remington's Pharmaceutical Sciences" by E. W. Martin (Mack Publishing Co., Easton, Pa.); Gennaro, A. R., Remington: The Science and Practice of Pharmacy, (Lippincott, Williams and Wilkins); Liberman, et al., Eds., Pharmaceutical Dosage Forms, Marcel Decker, New York, N.Y.; and Kibbe, et al., Eds., Handbook of Pharmaceutical Excipients, American Pharmaceutical Association, Washington.

The term "treat" as used herein refers to any type of treatment that imparts a benefit to a patient afflicted with a disease, including improvement in the condition of the patient (e.g., in one or more symptoms), delay in the progression of the condition, etc. In a particular embodiment, the treatment of a retroviral infection results in at least an inhibition/reduction in the number of infected cells.

A "therapeutically effective amount" of a compound or a pharmaceutical composition refers to an amount effective to prevent, inhibit, treat, or lessen the symptoms of a particular disorder or disease. The treatment of cancer herein may refer to curing, relieving, and/or preventing cancer, the symptom(s) of it, or the predisposition towards it.

As used herein, the term "therapeutic agent" refers to a chemical compound or biological molecule including, without limitation, nucleic acids, peptides, proteins, and antibodies that can be used to treat a condition, disease, or disorder or reduce the symptoms of the condition, disease, or disorder.

As used herein, the term "small molecule" refers to a substance or compound that has a relatively low molecular weight (e.g., less than 4,000, less than 2,000, particularly less than 1 kDa or 800 Da). Typically, small molecules are organic, but are not proteins, polypeptides, or nucleic acids, though they may be amino acids or dipeptides.

As used herein, the term "amphiphilic" means the ability to dissolve in both water and lipids/apolar environments. Typically, an amphiphilic compound comprises a hydrophilic portion and a hydrophobic portion. "Hydrophobic" designates a preference for apolar environments (e.g., a hydrophobic substance or moiety is more readily dissolved in or wetted by non-polar solvents, such as hydrocarbons, than by water). As used herein, the term "hydrophilic" means the ability to dissolve in water.

As used herein, the term "polymer" denotes molecules formed from the chemical union of two or more repeating units or monomers. The term "block copolymer" most simply refers to conjugates of at least two different polymer segments, wherein each polymer segment comprises two or more adjacent units of the same kind.

The following examples provide illustrative methods of practicing the instant invention, and are not intended to limit the scope of the invention in any way.

Example 1

Doxil®, a PEGylated liposomal formulation of small molecular anticancer drug, doxorubicin (DOX), has been extensively used in clinics for the treatment of various types of cancers (e.g., ovarian cancer, AIDS-Related Kaposi's sarcoma and multiple myeloma) (Amantea et al. (1997) Clin. Pharmacol. Ther., 61:301-311; Sharpe et al. (2002) Drugs 62:2089-2126; Gabizon et al. (2001) Cancer Invest., 19:424-436). However, the response rate of Doxil® single agent is limited and the combinations of Doxil® with other chemotherapeutic drugs (Taxol®, Hycamtin®) have been reported to be well tolerated by patients and have higher efficacy (Campos et al. (2003) Gynecol. Oncol., 90:610-618; Dunton, C. J. (1997) Semin. Oncol., 24:S5-2-S5-11). Thus, the studies of new Doxil® combination with other agents are of increasing interest for development of new cancer treatments. The amphiphilic block copolymers, Pluronics®, consisting of polyoxyethylene-polyoxypropylene blocks, were used in the instant study with several regimens of combinational therapies: pretreatment with block copolymers with subsequent administration of Doxil®, co-administration of Doxil® and Pluronic®, and Doxil® treatment with consequent post-treatment with Pluronic®. The cytotoxicity studies in ovarian cancer sensitive A2780 and resistant A2780/DOX as well as breast cancer sensitive and resistant cell lines, MCF7, MCF7/ADR, in vitro data indicates that co-administration with Doxil® pre-treatment or post-treatment cells with Pluronic® at nontoxic concentration, induced significant more nuclear uptake of DOX than Doxil® alone. DOX in vitro release profiles from Doxil® liposomes and fluorescence quenching analysis have revealed that Pluronic® induces the increase of mobility and permeability of liposomal lipid bilayer, which may attribute to the release of the drug from liposomes. Pluronic® 1 hour and 48 hours post treatments with Doxil® have shown significantly better antitumor activities than Doxil® alone group.

Combinations of well-characterized drugs that have been successfully used in clinics for the treatment of cancer patients with novel materials/activators, and use of novel treatment regimens may serve a solution and offer substantial advantages as compared to therapeutic molecules used alone. Doxil®, a PEGylated liposomal formulation of the anticancer drug doxorubicin, has been extensively used in phase I and phase II combination studies for the treatment of various types of cancers. The response rates of these combination, particularly in platinum-resistant ovarian cancer, were reported highly than single-agent PEGylated liposome doxorubicin (Rose et al. (2008) Am. J. Clin. Oncol., 31:476-480; Markman et al. (2004) Semin. Oncol., 31:91-105; Gabizon et al. (1994) Acta Oncol., 33:779-786; Eltabbakh et al. (2001) Expert Opin. Pharmacother., 2:109-124). However, the combination therapy is not deprived of side effects and the administration of more than one cytotoxic agent can result in even more severe systemic toxicity of the formulation in comparison to single agents. An ideal agent for combination therapy would have low systemic toxicity and have synergistic effect with the other drug in the formulation. Combinations of liposomal doxorubicin with ATP sensitizers for ovarian cancer have been reported (Di Nicolantonio et al. (2002) Anticancer Drugs, 13:625-630; Cree, I. A. (2003) Cancer Res., 161:119-125; Knight et al. (2009) BMC Cancer, 9:38). Pluronic® block copolymers are very potent chemosensitizer of mulidrug resistant (MDR) cancers (Batrakova et al. (2010) J. Control Release, 143:290-301; Batrakova et al. (2003) Pharm. Res., 20:1581-1590). Pluronic® block copolymers inhibit P-pg ATPase activity, a major protein associated with multidrug resistance in numerous cancers, responsible for efflux of cytotoxic drugs from the cells (Kabanov et al. (2003) J. Control Release, 91:75-83). Additionally, Pluronic® induces ATP depletion, inhibition of oxygen consumption, and inhibition of mitochondria respiratory chain complexes I and IV selectively in MDR cells. All together these effects significantly increase the cytotoxicity of doxorubicin in drug resistant cancers (Alakhova et al. (2010) J. Control Release, 142:89-100). Notably, SP1049C, the formulation of Pluronics® L61, F127 with doxorubicin has successfully completed Phase II clinical trial in advanced esophageal adenocarcinoma (Batrakova et al. J. Control Release, 130:98-106). Here, a novel therapeutic approach is provided for the treatment of cancer using a combination of liposomal doxorubicin, Doxil®, with Pluronic® block copolymer, and a treatment regimen that drastically enhances the anticancer efficiency of Doxil®.

Materials and Methods

Chemicals and Materials

Doxil® (DOX HCl liposome injection) was purchased from ALZA Corp (Mountain View, Calif.). ATP assay kit (#FLAA-1KT), Thiazolyl Blue Tetrazolium Bromide (MTT, #M5655-1G), Dulbecco's phosphate buffered saline solution (PBS) were purchased from Sigma-Aldrich (St. Louis, Mo.). Pluronic® P85 (lot #WPYE537B) was kindly provided by BASF Corporation (North Mount Olive, N.J.). A PEO/PPO/PEO monomer unit ratio is 26/40/26 in P85. Assay buffer is 122 mM sodium chloride, 25 mM sodium bicarbonate, 10 mM glucose, 10 mM HEPES, 3 mM potassium chloride, 1.2 mM magnesium sulfate, 1.4 mM calcium chloride and 0.4 mM potassium phosphate dibasic and adjusted to pH 7.4.

Cells and Culture Conditions

A2780, MCF7 were purchased from ATCC. A2780 and A2780/DOX were cultured in RPMI 1640 media, MCF7 and MCF7/ADR were cultured in DMEM media, with 10% Fetal Bovine Serum (Invitrogen, Carlsbad, Calif.), 100 U/ml penicillin, 100 mg/ml streptomycin. MCF7/ADR, A2780/DOX were cultured in the presence of 1 µg/ml DOX. Cells were grown at 37° C. in a humidified atmosphere of 5% $CO_2$ (v/v) in air. All experiments were performed on cells in the exponential growth phase.

Western Blot Assay

To identify P-glycoprotein (Pgp) phenotype of cells, immunoblots were performed. The monoclonal antibodies to Pgp, C219 (Dako Corp. Carpinteria, Calif.) were used at 1:100 dilutions. The monoclonal antibody to β-actin (Sigma Inc.) was used with a 1:15000 dilution. The secondary horseradish peroxide anti-mouse Ig antibodies (1:20000 dilution) was purchased from Sigma Inc.

Cytotoxicity Assay

Cells were seeded in 96-well plates at an initial density of $8 \times 10^3$ cells/well 24 hours prior to treatment. On the following day, cells were treated with DOX or Doxil® with or without 0.1% (w/v) P85 for 2 or 24 hours at 37° C. in a humidified, 5% $CO_2$ atmosphere. Following treatment, the medium was removed and the cells were rinsed three times by PBS and cultured for three days in fresh medium. The cytotoxicity was evaluated using a standard MTT assay and the absorbance was determined at 562 nm using SpectraMax M5®. Each concentration point was determined from samples from eight separate wells. $IC_{50}$ values were calculated based on the percentage ratio between treated cells and untreated control by using GraphPad Prism 5 Software (GraphPad Software, San Diego, Calif.).

Cellular Uptake Assay

Cells were seeded on 24 well-plate with the initial density of $8 \times 10^3$ cells/well, on the day of treatment, the cells were 70-80% confluent. After 2 or 24 hours incubation with or without 0.1% (w/v) Pluronic® P85, cells were rinsed three times with PBS, trypsinized, supplemented with 1 ml of complete media, and collected by centrifugation at 1500 rpm for 3 minutes. The cell pellet was re-suspended in 1 ml of PBS containing 1% BSA and analyzed for DOX fluorescence in UNMC cell analysis core facility.

Confocal Images

Cells were seeded 48 hrs prior treatments in 8-well chamber slides with an initial cell density of $1.0 \times 10^4$. Confluent cells were exposed to Doxil® (200 or 400 µg/ml) for 24 or 48 hours to identify the intracellular localization of DOX. Cell nuclei were additionally stained by Hoechst 33258 (Sigama, St. Louis, Mo.). Atto 647 labeled Pluronic® P85 was synthesized as described (Yi et al. (2010) Free Radic. Biol. Med., 49:548-558). 0.007% Atto 647 labeled P85 mixed with 0.1% unlabeled P85 were used to investigate the colocalization of Pluronic® and cytoplasm. Cells were then visualized utilizing live cell confocal imaging (Carl Zeiss LSM 510 Meta, Peabody, Mass.).

Release Studies of Doxil®

Effect of P85 on release of DOX from Doxil® was studied by dialysis method using a membrane (MW cut-off 3,500 Da). 1 ml of Doxil® solution with DOX concentration of 0.2 mg/ml in phosphate buffered saline were placed into a dialysis bags and dialyzed against 25 ml of PBS under continuous shaking at 37° C. in dark. 1 ml samples of the dialysate solution were withdrawn at a definite time interval (1, 2, 4, 8 and 24 hours) and replaced with an equal volume of fresh media. The concentration of DOX in the dialysate samples was determined by measuring absorbance at 485 nm using Lambda 25 UV/VIS spectrophotometer. The amount of DOX released from Doxil® was expressed as a percentage of the total DOX and plotted as a function of time.

Fluorescence Studies

Fluorescence spectra of free DOX and Doxil® liposome in the presence of 0.1% Pluronic® P85 were recorded using a spectrofluorometer system (Flourlog®, HORIBA Jobin Yvon Inc., NJ) at wavelength of 480 nm with the bandwidth of 5 nm of excitation and emission. Solutions of free DOX and Doxil® used for these studies were at 50 µM equivalent concentrations of DOX. Fluorescence measurement for Tritc-labeled P85 was performed at $\lambda_{ex}=550$ nm with the bandwidth of 2 nm for excitation and emission.

Size and ζ-Potential Measurements

Zetasizer (Marvern Instruments Limited. U.K) was used to determine effective hydrodynamic diameters (Deff) and zeta-potential of the particles at 25° C. Software provided by the manufacturer was used to analyze the size of the particles, polydispersity indices and zeta-potential of liposomes. The mean values were calculated from the measurements performed at least in triplicate.

Animals

All experiments were carried out with the approval of the University of Nebraska Medical Center Institutional Animal Care and Use Committee and in accordance with the NIH Guide for Laboratory Animal Use. Athymic nu/nu mice (6- to 8-weeks-old females, National Cancer Institute, Frederick, Md.) were used to generate the tumor model throughout this study. The animals were kept in groups of five and fed ad libitum.

Animal Tumor Model and Antitumor Activity

Human ovarian carcinoma xenografts were used as previous described (Pakunlu et al. (2006) J. Control Release, 114:153-162; Wang et al. (2008) Clin. Cancer Res., 14:3607-3616). A2780 human ovarian cancer cells ($4.0 \times 10^6$) were subcutaneously (s.c.) injected into the right flanks of female athymic nu/nu mice. When the tumors reached a size of about 0.5 $cm^3$ (10-15 days after transplantation), mice were given intravenous (i.v.) injections via the tail vein with Doxil® (12 mg DOX/kg for the single injection). In the post treatment groups, 1 hour or 48 hours later, the mouse were treated with 0.02% (w/v) P85 as the same volume of Doxil® as they were administrated before. Animal weight and tumor volume was measured every other day. The tumor length (L) and width (W) were calculated by equation: $WR = \frac{1}{2} \times L \times W^2$.

Statistical Analysis

The differences between treatment groups were analyzed by using student's t-test for pairs of groups and one-way analysis of variance (ANOVA) for multiple groups. The p-value less than 0.05 were considered statistically significant. All statistical analyses were carried out using GraphPad Prism Software (Version 5.0, GraphPad Software, San Diego Calif., USA).

Results

Effect of Pluronic on in vitro Cytotoxicity of Doxil® Cancer Cells

For the majority of the studies, the sensitive and multidrug resistant (MDR) ovarian cancer cells, A2780 and A2780/DOX were used. Selected studies were also done using sensitive and MDR breast adenocarcinoma cells, MCF7 and MCF7/ADR. First, cells were exposed to increasing concentrations of Doxil® for 2 hours in the presence or absence of P85 (0.1% w/v). As shown in Table 1, at 2 hours exposure Doxil® alone at concentrations up to 200 mg/ml (counting per Dox contained in the liposome formulation) did not induce cytotoxicity in either ovarian cancer cell line. However, co-treatment with P85 increased Doxil® cytotoxicity in both sensitive and resistant cancer cells. 2 hours exposures to 0.1% P85 alone did not induce cytotoxicity in the same cells. Similar results were obtained for breast cancer cells (Table 2).

TABLE 1

$IC_{50}$ values (μg/mL) of Doxil ® in ovarian cancer cells upon different treatments.

| Treatment | Doxil ® $IC_{50}$, μg/ml [a] | |
|---|---|---|
|  | A2780 | A2780/DOX |
| Doxil ®(2 hrs) | N.D.* | N.D.[e] |
| Doxil ® + 0.1% P85 (2 hrs, co-exposure)[b] | 7.55 ± 0.36 | 8.32 ± 0.56 |
| Doxil ®(24 hrs) | 48.02 ± 4.85 | N.D.[e] |
| Doxil ®(24 hrs) + 0.1% P85 (2 hrs, pre-exposure)[c] | 17.48 ± 1.14 (**) | N.D.[e] |
| Doxil ®(24 hrs) + 0.1% P85 (2 hrs, post-exposure)[d] | 14.76 ± 3.24 (**) | N.D.[e] |

[a] Experiments were performed in quadruplicate and data is expressed as means ± SEM of at least 4 independent experiments.
N.D. non-detectable up to 200 μg/ml.
Statistical comparisons were made by t-test between Doxil ® (24 hours) and either of the pre- or post-exposure groups:
(**) p < 0.05.
[b] Cells were co-incubated for 2 hours with Doxil ® and 0.1% P85, washed three times with PBS, and grown in fresh medium for 72 hours before measuring cytotoxicity.
[c] Cells were first treated with 0.1% P85 for 2 hours, washed three times with PBS, further incubated with Doxil ® for 24 hours, washed three times with PBS, and grown in fresh medium for 72 hrs before measuting cytotoxicity.
[d] Cells were first treated with Doxil ® for 24 hours, washed three times with PBS, followed by 2 hours treatment with 0.1% P85.

TABLE 2

$IC_{50}$ values (μg/mL) of Doxil ® in breast cancer cells upon different treatments. See Table 1 for description.

| Treatment | Doxil ® $IC_{50}$, μg/ml [a] | |
|---|---|---|
|  | MCF7 | MCF7/ADR |
| Doxil ®(2 hrs) | N.D.* | N.D.[e] |
| Doxil ® + 0.1% P85 (2 hrs, co-exposure)[b] | 43.24 ± 0.38 | 52.49 ± 0.73 |
| Doxil ®(24 hrs) | 6.24 ± 0.26 | N.D. |
| Doxil ®(24 hrs) + 0.1% P85 (2 hrs, pre-exposure)[c] |  | N.D. |
| Doxil ®(24 hrs) + 0.1% P85 (2 hrs, post-exposure)[d] | N.D. |  |

The effects P85 on Doxil® cytotoxicity was examined upon 24 hours exposure. To avoid P85 toxicity the copolymer was added to cells for 2 hours only either immediately before or after exposure to Doxil®. This also allowed for the exclusion of the direct interaction between P85 and Doxil® in the exposure media. Doxil® alone, at 24 hours exposure displayed toxicity in sensitive but not resistant cell lines (Tables 1 and 2). The pretreatment and post treatment with P85 also increased cytotoxicity of Doxil® in A2780 cell line, compared to Doxil® alone group.

Effect of Pluronic® on Drug Uptake in Cancer Cells

Intracellular accumulation of Doxil® was examined by FACS analysis. This method did not allow for distinguishing between Dox incorporated into or released from the Doxil® particles, but provided a good measure of total Dox fluorescence in cells. Cells were exposed to Doxil® for 2 hours or 24 hours. P85 was added exactly as in the cytotoxicity experiments described above: either concurrently with Doxil® in the case of 2 hours exposures, or for 2 hours before or after Doxil® in the case of 24 hours exposures. In each case, except for pre-exposure in MDR cells, 0.1% P85 resulted in significant increases in drug intracellular accumulation (FIGS. 1A and 1B). In a similar experiment, cells were lyzed and Dox fluorescence was normalized to the amount of cell protein. The overall results were similar to the FACS study (FIG. 2), which demonstrates that results are changes in the net uptake of the drug rather than its redistribution inside cells between the free and liposome bound forms, which have different fluorescence.

The P85 induced increases in the drug uptake were most pronounced in the case of co-treatment, when both the copolymer and Doxil® were present in the cell culture medium simultaneously. This indicated that P85 co-exposure with Doxil® promoted the release of the drug from the liposome. This trend was seen in both sensitive and MDR cells. It is interesting to note, that in the MDR cells the levels of the drug uptake were considerably less than those in sensitive cells (FIGS. 1A and 1B). This may be due to either lower rate of internalization of Doxil® particles or rapid efflux of free Dox released from the liposomes internalized inside the cells. Since, P85 is an inhibitor of the P-glycoprotein (Pgp) efflux pump, it is likely that one of its activities included inhibition of Dox efflux in the MDR cells. This was most likely to happen in the conditions of the co-treatment of Doxil® with P85, which were most favorable for the copolymer's induced drug release and efflux inhibition. As a result under these conditions, the differences in uptake between sensitive and resistant cells were greatly reduced. The conditions of pre-treatment with P85 after 24 hours exposure to Doxil® appeared to be less likely to affect drug release and efflux, which may explain lower P85 effect of drug uptake in MDR cells.

Cellular Trafficking of Doxil® in Cancer Cells in the Absence and Presence of Pluronic®

Intracellular localization of drugs plays crucial role in their activity and toxicity. DOX works via intercalation into DNA and inhibition of topoisomerase II, which unwinds DNA for transcription and thus stopping the replication process (Gewirtz, D. A. (1999) Biochem. Pharmacol., 57:727-741). Therefore it is important that DOX reaches the nucleus. Uptake of liposomal DOX, Doxil®, is rather slow process and after 24 hours of exposure to 200 μg/ml Doxil® the uptake is low and DOX fluorescence is seen in intracellular vesicles with no nuclear localization (FIG. 3A). However, 0.1% Pluronic® P85 together with Doxil® drastically increased the DOX cellular uptake and nuclear translocation in both drug sensitive and resistant cells (FIG. 3A). In the presence of 0.1% Pluronic® the drug uptake by the cells was observed as early as after 5 minutes and is quickly translocated to the nucleus (FIG. 3B). Intracellular localization of P85 was observed using Atto647 labeled Pluronic. The cells were treated with 0.007% of labeled polymer supplemented with 0.1% of unlabeled Pluronic® (FIG. 3A).

The effect of post-treatment with 0.1% P85 on Doxil®/DOX trafficking was further studied in A2780 cells (FIG. 3C). The cells were incubated with 200 μg/ml Doxil® for 24 hours, washed, and 0.1% P85 was added for 1 hour. After 60 minutes incubation with Pluronic there was little if any colocalization with DOX from Doxil®. 24 hours later some co-localization was observed, however there was no nuclear uptake of the drug. Next the incubation with Doxil® was extended to 48 hours, pre- and post-treatment of P85 with 2 hours and localization could be observed in FIG. 3C.

Fluorescence Quenching Analysis of DOX Fluorescence in Doxil® with and without 0.1% P85

DOX exists in a crystalline state inside the Doxil® liposome and therefore its fluorescence is quenched (by ca. 82%). Upon the release of the drug the fluorescence emission is increased. The fluorescence intensity of Doxil® was measured in the presence and absence of 0.1% P85 to evaluate the release of DOX from the liposomes. Fluorescence emission of Doxil® alone was not changed over the time period of 1 hour. Upon addition of Pluronic®, drastic increase of fluorescence was seen after 30 minutes of incubation and did not change during the following 30 minutes indicating that the release was fast and reached its maximum during first 30 minutes of exposure to Pluronic® (FIG. 4).

The effect of Pluronic® on doxorubicin release from DOXIL® in vitro was also determined. As seen in FIG. 5, doxorubicin was released from the liposomes at higher rates in the presence of Pluronic® both at pH 5.5 and 7.4.

Anti-Tumor Efficacy of Doxil® and Pluronic P85 Formulations

Antitumor effects of Doxil® in the presence or absence of Pluronic® formulation were evaluated to determine whether Pluronic® could enhance the drug accumulation in the tumor and lead to tumor suppression. A2780 ovarian tumor bearing mice received i.v. with 12 mg/kg single injection of Doxil®. One hour, 48 hours and 96 hours later, mice were received the same amount of 0.02% P85 after Doxil® administration. The tumor volumes were measured every other day. Tumor volume changes in control and treated groups are shown in FIG. 6. Post treatment of Pluronic P85 induced significant tumor growth inhibition compared to the single dose of Doxil®, even in the 1 hour post treatment group. The anti-tumor efficacy was more pronounced in the 48 hours post treatment group. The observed difference in anti-tumor effects of Doxil® in the presence or absence of Pluronic® could be correlated to the pharmacokinetic characteristic of Doxil®, which is well known as the long blood circulation of DOX. As it was demonstrated above (FIG. 4), Pluronic® induces the increase of mobility and permeability of liposomal lipid bilayer, which attribute to the rapid release of the drug from liposomes.

To evaluate the systemic toxicity of different treatments heart, liver, spleen and kidneys were isolated from tumor bearing animals at the end point of the experiment. The histological analysis (FIG. 7) did not show any toxicity in all cases.

Example 2

Pluronic® P85 (P85) was administered either 48 or 96 hours after Doxil®, which corresponded to the greatest increase or no change of anti-tumor activity, respectively. The animals were sacrificed 1 or 6 hours after administration of the copolymer and the drug fluorescence in the tumor sections was analyzed. The blood vessels (CD31) and nucleus (DAPI) were also stained for reference. As seen from fluorescence analysis, following administration of P85 at the 48 hours time point the overall fluorescence of Dox in tumor sections greatly increased compared to DOXIL® alone (FIG. 8A). This effect was most pronounced 6 hours after the copolymer administration. Notably, in the absence of P85 the drug fluorescence was mainly co-localized with blood vessels, while after addition of P85 the drug became spread throughout the tumor reaching distal areas. This indicated that at 48 hours DOXIL® particles were deposited mainly in the blood vessels, while the block copolymer P85 promoted the release of Dox from the liposomes in the tumor tissue. The whole tumor images clearly reinforced increased drug fluorescence in the tumors after administration of the copolymer (FIG. 8C, upper panel). However, a strikingly different picture was observed when the copolymer was injected 96 hours after Doxil®. In this case the drug appeared to be already released from the liposomes and its fluorescence in the tumors did not change after injection of the copolymer (FIG. 8C, lower panel).

Analysis of drug disposition to the tumor by HPLC indicates that P85 had induced small albeit significant increase in the drug levels 6 hours after the copolymer administration when the copolymer was administered 48 hours after Doxil® (FIG. 8B). The maximal accumulation of the drug in the solid tumors in mouse is observed between 24 and 48 hours (Laginha et al. (2005) Clin. Cancer Res., 11:6944-6949). Therefore, administration of the copolymer after Doxil® at the time point corresponding to the maximal accumulation of the drug in the solid tumor results increased levels of drug in the tumor, enhance release of the drug throughout the tumor, and as shown above also increases anti-tumor activity. In contrast, administration of the copolymer too early such as 1 hour after Doxil® or too late such as 96 hours after Doxil® does not result in as significantly improved release of the drug in the tumor and does not as significantly improve anti-tumor effect.

Materials and Methods

Animal Treatment

Same as Example 1

Immunohistochemistry

Immunohistochemical analyses were performed on tumor sections derived from A2780-bearing nude mice. Tumors derived from untreated mice or from those treated with Doxil®, administered either alone or in combination with P85. Paraffin-embedded formalin fixed tissue sections were either stained with Mayer's H&E (Sigma Chemical Co., St. Louis, Mo.) or FITC-labeled CD31 antibody (BD Biosciences, diluted 1:100). All staining procedures ended with a 5 minute application of Hoechst 33342 (Sigma-Aldrich, St. Louis, Mo.) to counterstain for cellular nuclei. The slides were mounted and pictures were taken under a fluorescence microscope (Zeiss Axioplan 2 imaging microscope).

Example 3

Considerable amounts of Doxil® is still circulating in the blood at 48 hours. There is no direct method for measuring separately the free and liposome-incorporated drug in the plasma as the HPLC assay provides the total amount of the extracted drug. Administration of P85 at 48 hours practically did not change the subsequent drug pharmacokinets profile, which remained similar to that of Doxil® alone (FIG. 9). This indicates that post-injection of Pluronic® did not release the drug from circulating Doxil® liposomes since free Dox would have been rapidly cleared from the blood. Thus, administration of the block copolymer after the Doxil® does not release of drug from the circulating liposomes, but as shown above in Example 2 it releases the drug deposited in the tumors.

Materials and Methods

Animal Treatment

Same as Example 1

Plasma Drug Distribution

Six-week old female BALB/c mice were purchased from Charles River Breeding Laboratories (Raleigh, N.C., USA).

Mice were treated with a single i.v. injection of 12 mg/kg of Doxil®. P85 (0.02%, 100 µL/mice) was administered i.v. 48 hours after the drug, animals were sacrificed and blood samples were collected every 12 hours after the treatments, followed by the HPLC and hematologic analysis.

HPLC Analysis

Dox concentration in tumor tissue samples and plasma were determined using HPLC method. Before analysis, the tumor tissues were firstly homogenized using a tissue TEAROR® equipped with a 7 mm probe (Biospec Products, Inc.). The tissues were diluted 1:1 (w/v) with HPLC grade water, and homogenized. For 40 µL tissue homogenate or plasma, 8 µL daunomycin (0.2 mg/mL) was used as an internal standard (IS). The frozen sample was lyophilized using a vacuum freeze drier (FreeZone 2.5 liter, Labconco Inc., Kansas City, Mo.). For each sample, Trichloroacetic acid (TCA, 10%) 100 µL were added prior being vortex-mixed for 30 seconds. Samples were centrifuged at 15,000 g for 10 minutes at 4° C. The supernatant (80 µL) was transferred into a tube and evaporated to dryness for 2 hours under a stream of gas in a 40° C. heating pad. The residue was reconstituted in 80 µL of the mobile phase, and a 60 µL aliquot was used for HPLC analysis. The tissue was determined using a reversed-phase C18 column (Agilent Eclipse XDB, 150×4.6 mm i.d., 5 µm particle size) and Agilent 1200 HPLC system (G1353B UV detector, G1321A fluorescence detector, G1311A pump, G1329A Autosampler, G1316A column oven) at flow rate of 1.2 mL/min. The mobile phase was: 1.0% acetic acid: acetonitrile solution=48%:52%. Fluorescence detection of Dox was carried out at $\lambda_{ex}$=480 nm and $\lambda_{em}$=590 nm.

Example 4

The effect of Pluronic® copolymers on the release of Dox from Doxil® were studied by a dialysis method using a membrane (MW cut-off 3,500 Da). Stock solution of Doxil® (with Dox 2 mg/mL) was diluted 10 times in the presence or absence of P85 in either PBS, pH 7.4 or 50 mM acetate buffer, pH 5.5. The resulting solutions of Doxil® with/without Pluronic® copolymers (1 mL) were placed into dialysis bags and dialyzed against 25 mL of the corresponding buffer under continuous shaking at 37° C. in dark. Samples (1 mL) of the dialysate solution were withdrawn at definite time points (1, 2, 4, 8, 24 and/or 48 hours) and replaced with an equal volume of fresh buffer. The concentration of Dox in the dialysate samples was determined by measuring absorbance at 485 nm using Lambda 25 UV/VIS spectrophotometer (PerkinElmer). The amount of Dox released from Doxil® was expressed as a percentage of the total Dox and plotted as a function of time.

Studying the drug release by the method of equilibrium dialysis indicated that the addition of different Pluronic® copolymers (P85, F127, L61, F68) to Doxil® dispersion at either pH5.5 or pH7.4 substantially increased the release rate of Dox (FIG. 10). In this case about 50% of the drug was released during the study period in Pluronic® P85 (FIG. 10A, 10B), or other Pluronic® copolymers (FIG. 10C, 10D) while the release of the drug from Doxil® alone was less than 15%. Notably, the ability of P85 to release the drug from the liposomes was dependent on the concentration of the copolymer. Specifically, the release enhancement was relatively strong with 0.02% to 0.5% P85, considerably less with 0.001% P85 and virtually non-existing with 0.0001% P85 (FIG. 10A, 10B).

At the concentration of 0.02 wt. %, similar to Pluronic® P85, Pluronic® F127 as well as the mixture of Pluronic® L61 and F127 (1:8 wt) dramatically increased the drug release from the liposome—about 50% of the drug was released during 48 hours while Doxil® alone was released less than 15%. Pluronic® F68 having has lesser effect on the drug release from Doxil® (FIG. 10C, 10D). Thus the highest drug release potency is shown by copolymers having greatest content of PPO (about 30% in Pluronic® F127, or about 50% in Pluronic® P85, or about 90% in Pluronic® L61), and by copolymers having the greater molecular mass of PPO block (about 2,250 in Pluronic® P85, about 3,800 in Pluronic® F127). The lowest potency is displayed by the copolymer having the lowest content of PPO (about 20% in Pluronic® F68) and the lower molecular mass of PPO block (about 1,740). The molecular masses of the PPO and PEO blocks and their weight percent in the block copolymers are provided in the literature and are proportional to the number of the propylene oxide and ethylene oxide units in the respective blocks (Kabanov et al. (2002) J. Control. Release 82:189-212). The molecular masses of the propylene oxide and ethylene oxide units are 58 and 44, respectively. It is also noteworthy that the greatest potency is shown by relatively more hydrophobic copolymers having the hydrophilic-lipophilic balance (HLB) of about 22 and less (HLB 22 for Pluronic® F127, HLB 16 for Pluronic® P85, and HLB 3 for Pluronic® L31), while the lowest potency is shown by the hydrophilic block copolymer having HLB higher than 22 (HLB 29 for Pluronic® F68). It is also noteworthy that the most potent block copolymers have the lowest critical micelle concentration (CMC) at 37° C. of no more than about 0.0028 mM for Pluronic® F127, or about 0.065 mM for Pluronic® P85, or about 0.11 mM for Pluronic® L61, while the lowest potency is shown by the hydrophilic block copolymer Pluronic® F68 having the CMC of about 0.48 mM. The values of HLB, CMC, the conditions and methods for their measurements and their relationships to the lengths of the PPO and PEO blocks can be found in literature (Batrakova et al. (1999) Pharm. Res., 16:1373-1379; Kozlov et al. (2000) Macromolecules 33:3305-3313; Kabanov et al. (2002) J. Control. Release, 82:189-212).

Notably, the size and polydispersity of the liposomes in the presence of even highest concentration of P85 did not change for the same time period (Table 3), indicating that the increased drug release was not associated with the disruption of the liposomes. At the same time, when Tritc-labeled P85 (Tritc-P85) was mixed with empty PEGylated liposomes, the fluorescence of Tritc was immediately quenched (ca. 50%), suggesting that the copolymer incorporated into the liposomal membrane (FIG. 11).

The ability of P85 to increase the rate of Dox diffusion across planar lipid and liposomal membranes without affecting the overall integrity of these membranes is described. The block copolymer greatly increased the rate of the release of Dox from the Doxil® liposomes. Moreover, the copolymer was shown here to have no effect on the liposome size. Yet it was capable of incorporating into the membranes, which presumably involves penetration of hydrophobic PPO chains in the nonpolar regions of the lipid bilayers. Hydrophobic Pluronics® insert in the lipid membranes and loosen the lipid packing during initial embedding below the lipid head groups, thereby acting as membrane permeabilizers.

TABLE 3

The size and PDI of Doxil ® liposomes after addition of P85 are provided. The effective hydrodynamic diameters ($D_{eff}$) and polydispersity indexes (PDI) of the particles in the Doxil ® dispersions (0.2 mg/mL counting per Dox contained in Doxil ®) supplemented with various concentrations of P85 at pH 5.5 or pH 7.4 and dialyzed for 24 hours against acetate buffer or PBS. The $D_{eff}$ and PDI were measured by photon correlation spectroscopy in a thermostatic cell at a scattering angle of 90° using the same instrument equipped with a Multi Angle Sizing Option (BI-MAS).

|  | Deff | PDI |
|---|---|---|
| Doxil ® (pH 5.5) | 83.9 ± 2.20 | 0.036 ± 0.01 |
| Doxil ® (pH 7.4) | 82.9 ± 1.21 | 0.011 ± 0.01 |
| Doxil ® + 0.5% P85 (pH 5.5) | 89.8 ± 0.44 | 0.032 ± 0.01 |
| Doxil ® + 0.5% P85 (pH 7.4) | 87.1 ± 0.68 | 0.067 ± 0.01 |
| Doxil ® + 0.1% P85 (pH 5.5) | 88.2 ± 1.07 | 0.067 ± 0.01 |
| Doxil ® + 0.1% P85 (pH 7.4) | 85.5 ± 0.91 | 0.067 ± 0.01 |
| Doxil ® + 0.02% P85 (pH 5.5) | 88.1 ± 0.95 | 0.049 ± 0.01 |
| Doxil ® + 0.02% P85 (pH 7.4) | 85.5 ± 0.73 | 0.067 ± 0.01 |
| Doxil ® + 0.01% P85 (pH 5.5) | 88.6 ± 0.06 | 0.036 ± 0.01 |
| Doxil ® + 0.01% P85 (pH 7.4) | 86.8 ± 0.47 | 0.046 ± 0.01 |
| Doxil ® + 0.001% P85 (pH 5.5) | 88.0 ± 0.25 | 0.058 ± 0.01 |
| Doxil ® + 0.001% P85 (pH 7.4) | 84.8 ± 0.94 | 0.059 ± 0.01 |
| Doxil ® + 0.0001% P85 (pH 5.5) | 87.2 ± 0.36 | 0.056 ± 0.01 |
| Doxil ® + 0.0001% P85 (pH 7.4) | 85.2 ± 1.07 | 0.027 ± 0.02 |

A number of publications and patent documents are cited throughout the foregoing specification in order to describe the state of the art to which this invention pertains. The entire disclosure of each of these citations is incorporated by reference herein.

While certain of the preferred embodiments of the present invention have been described and specifically exemplified above, it is not intended that the invention be limited to such embodiments. Various modifications may be made thereto without departing from the scope and spirit of the present invention, as set forth in the following claims.

What is claimed is:

1. A method of inhibiting a cancer in a subject, said method comprising co-administering at least one encapsulated chemotherapeutic agent and at least one amphiphilic block copolymer to said subject,
    wherein said method comprises administering to said subject said encapsulated chemotherapeutic agent before said amphiphilic block copolymer, wherein said encapsulated chemotherapeutic agent is administered about 1 hour to about 48 hours before said amphiphilic block copolymer,
    wherein said amphiphilic block copolymer comprises at least one block of ethylene oxide and at least one block of propylene oxide, and
    wherein said encapsulated chemotherapeutic agent is a PEGylated liposomal formulation comprising doxorubicin.

2. The method of claim 1, wherein said amphiphilic block copolymer is a poly(ethylene oxide)-poly(propylene oxide)-poly(ethylene oxide) triblock copolymer.

3. The method of claim 2, wherein the poly(propylene oxide) content of the amphiphilic block copolymer is at least 30%.

4. The method of claim 2, wherein the molecular mass of the poly(propylene oxide) block is from about 1200 to about 4200.

5. The method of claim 1, comprising the administration of a first amphiphilic block copolymer and a second amphiphilic block copolymer, wherein the first and second amphiphilic block copolymers are different.

6. The method of claim 1, wherein said amphiphilic block copolymer has a hydrophilic-lipophilic balance of about 22 or less.

7. The method of claim 1, wherein said cancer is a solid tumor.

8. The method of claim 1, wherein said cancer is breast cancer or ovarian cancer.

* * * * *